US011634499B2

(12) United States Patent
Larmore et al.

(10) Patent No.: US 11,634,499 B2
(45) Date of Patent: Apr. 25, 2023

(54) CONTROL OF TRACE METALS DURING PRODUCTION OF ANTI-CD38 ANTIBODIES

(71) Applicant: Janssen Biotech, Inc., Horsham, PA (US)

(72) Inventors: Nicole Larmore, Malvern, PA (US); Balasubramanian Ramanathan, Malvern, PA (US); Richard Yeager, Malvern, PA (US)

(73) Assignee: Janssen Biotech, Inc., Horsham, PA (US)

( * ) Notice: Subject to any disclaimer, the term of this patent is extended or adjusted under 35 U.S.C. 154(b) by 611 days.

(21) Appl. No.: 16/682,551

(22) Filed: Nov. 13, 2019

(65) Prior Publication Data

US 2020/0148782 A1 May 14, 2020

Related U.S. Application Data

(60) Provisional application No. 62/760,782, filed on Nov. 13, 2018.

(51) Int. Cl.
C07K 16/28 (2006.01)
C07K 1/14 (2006.01)
C07K 16/06 (2006.01)

(52) U.S. Cl.
CPC ............ *C07K 16/2896* (2013.01); *C07K 1/14* (2013.01); *C07K 16/065* (2013.01); *C12Y 302/01035* (2013.01)

(58) Field of Classification Search
CPC ....... C07K 16/2896; C07K 1/14; C12N 15/09
See application file for complete search history.

(56) References Cited

U.S. PATENT DOCUMENTS

| | | | |
|---|---|---|---|
| 4,072,565 A | 2/1978 | Weiss et al. | |
| 4,560,655 A | 12/1985 | Baker | |
| 4,615,977 A | 10/1986 | Hasegawa et al. | |
| 4,786,599 A | 11/1988 | Chessebeuf et al. | |
| 5,122,469 A | 6/1992 | Mather et al. | |
| 5,705,364 A | 1/1998 | Etcheverry et al. | |
| 5,856,179 A | 1/1999 | Chen et al. | |
| 5,976,833 A | 11/1999 | Furukawa et al. | |
| 6,048,728 A | 4/2000 | Inlow et al. | |
| 6,171,825 B1 | 1/2001 | Chan et al. | |
| 6,180,401 B1 | 1/2001 | Chen et al. | |
| 6,528,286 B1 | 3/2003 | Ryll | |
| 6,924,124 B1 | 8/2005 | Singh | |
| 9,550,826 B2 | 1/2017 | Labkovsky et al. | |
| 2007/0212770 A1 | 9/2007 | Grillberger et al. | |
| 2008/0009040 A1 | 1/2008 | Grillberger et al. | |
| 2009/0076249 A1 | 3/2009 | De Weers et al. | |
| 2012/0276631 A1 | 11/2012 | Bengea et al. | |
| 2018/0087080 A1 | 3/2018 | Nair et al. | |

FOREIGN PATENT DOCUMENTS

| | | |
|---|---|---|
| WO | WO-1988/01649 A1 | 3/1988 |
| WO | WO-1992/01047 A1 | 1/1992 |
| WO | WO-1994/13804 A1 | 6/1994 |
| WO | WO-1998/44001 A1 | 10/1998 |
| WO | WO-2004/078140 A2 | 9/2004 |
| WO | WO-2007/077217 A2 | 7/2007 |
| WO | WO-2009/085462 A1 | 7/2009 |
| WO | WO-2012/149197 A2 | 11/2012 |
| WO | WO-2015/130728 A1 | 9/2015 |
| WO | WO-2020/100073 A1 | 5/2020 |

OTHER PUBLICATIONS

Chothia, C. and Lesk, A.M., Canonical structures for the hypervariable regions of; Immunoglobulins, J. Mol. Biol., 196(4):901-17 (1987).
Gramer, M. et al., Modulation of Anitbody Galactosylation Through Feeding of Uridine, Manganese Chloride, and Galactose, Biotechnology Bioeng., 108:1591-1602 (2011).
Honegger, A. and Pluckthun, A., Yet another numbering scheme for immunoglobulin variable domains: an automatic modeling and analysis tool, J Mol Biol., 309(3):657-70 (2001).
International Search Report for PCT/IB19/59766, 4 pages (dated Feb. 28, 2020).
Knappik, A. et al., Fully synthetic human combinatorial antibody libraries (HuCAL) based on modular consensus frameworks and CDRs randomized with trinucleotides, J. Mol. Biol., 296(1):57-86 (2000).
Lefranc, M. et al., IMGT unique numbering for immunoglobulin and T cell receptor variable domains and Ig superfamily V-like domains, Dev Comp Immunol., 27(1):55-77 (2003).
Luo, Y. and Chen, G., Combined approach of NMR and chemometrics for screening peptones used in the cell culture medium for the production of a recombinant therapeutic protein, Biotechnol Bioeng., 97(6):1654-9 (2007).
Martin, A.C., and Thornton, J.M., Structural families in loops of homologous proteins: automatic classification, modelling and application to antibodies, J Mol Biol., 263(5):800-15 (1996).
Pacis, E. et al., Effects of Cell Culture Conditions on Antibody N-linked Glycosylation—What Affects High Mannose 5 Glycoform, Biotechnology and Bioengineering, 108(10):2348-2358 (2011).
Prabhu, A. and Gadgil, M., Nickel and cobalt affect galactosylation of recombinant IgG expressed in CHO cells, Biometals, 32:11-19 (2019).
Radhakrishnan, D. et al., Controlling the Glycosylation Profile in mAbs Using Time-Dependent Media Supplementation, Antibodies, 7(1):1-21 (2018).
Shi, L. et al., De novo selection of high-affinity antibodies from synthetic fab libraries displayed on phage as pIX fusion proteins, J Mol Biol., 397(2):385-96 (2010).
St. Amand, M., et al., Identification of Manipulated Variables for a Glycosylation Control Strategy, Biotechnology and Bioengineering, 111(10):1957-1970 (2014).

(Continued)

*Primary Examiner* — Prema M Mertz
(74) *Attorney, Agent, or Firm* — Choate, Hall & Stewart LLP; Rolando Medina; Meaghan E. Bychowski

(57) ABSTRACT

The disclosure relates to methods to control trace metals during production of anti-CD38 antibodies, drug substances and drug products generated using the methods, and uses of the generated drug substances and drug products.

77 Claims, 6 Drawing Sheets

Specification includes a Sequence Listing.

(56) References Cited

OTHER PUBLICATIONS

Surve, T. and Gadgil, M., Manganese Increases High Mannose Glycoform on Monoclonal Antibody Expressed in CHO When Glucose is Absent or Limiting: Implications for Use of Alternate Sugars, Biotechnol. Prog., 31(2):460-467 (2015).
Written Opinion for PCT/IB19/59766, 8 pages (dated Feb. 28, 2020).
Wu, T. and Kabat, E., An analysis of the sequences of the variable regions of Bence Jones proteins and myeloma light chains and their implications for antibody complementarity, J Exp Med., 132(2):211-50 (1970).

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: daratumumab HCDR1

<400> SEQUENCE: 1
```

```
Ser Phe Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: daratumumab HCDR2

<400> SEQUENCE: 2

Ala Ile Ser Gly Ser Gly Gly Thr Tyr Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: daratumumab HCDR3

<400> SEQUENCE: 3

Asp Lys Ile Leu Trp Phe Gly Glu Pro Val Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: daratumumab LCDR1

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: daratumumab LCDR2

<400> SEQUENCE: 5

Asp Ala Ser Asn Arg Ala Thr
1               5

<210> SEQ ID NO 6
<211> LENGTH: 10
<212> TYPE: PRT
<213> ORGANISM: Artificial Sequence
<220> FEATURE:
<223> OTHER INFORMATION: daratumumab LCDR3

<400> SEQUENCE: 6

Gln Gln Arg Ser Asn Trp Pro Pro Thr Phe
1               5                   10

<210> SEQ ID NO 7
<211> LENGTH: 122
<212> TYPE: PRT
<213> ORGANISM: Artificial Sequence
<220> FEATURE:
<223> OTHER INFORMATION: daratumumab VH

<400> SEQUENCE: 7
```

-continued

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
            115                 120

<210> SEQ ID NO 8
<211> LENGTH: 107
<212> TYPE: PRT
<213> ORGANISM: Artificial Sequence
<220> FEATURE:
<223> OTHER INFORMATION: daratumumab VL

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 9
<211> LENGTH: 452
<212> TYPE: PRT
<213> ORGANISM: Artificial Sequence
<220> FEATURE:
<223> OTHER INFORMATION: daratumumab HC

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Phe Cys
                    85                  90                  95
Ala Lys Asp Lys Ile Leu Trp Phe Gly Glu Pro Val Phe Asp Tyr Trp
                100                 105                 110
Gly Gln Gly Thr Leu Val Thr Val Ser Ser Ala Ser Thr Lys Gly Pro
                115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Arg Val Glu Pro Lys Ser
                210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser Thr
                290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly Lys
        450

<210> SEQ ID NO 10
<211> LENGTH: 214
<212> TYPE: PRT
<213> ORGANISM: Artificial Sequence
```

-continued

<220> FEATURE:
<223> OTHER INFORMATION: daratumumab LC

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 120
<212> TYPE: PRT
<213> ORGANISM: Artificial Sequence
<220> FEATURE:
<223> OTHER INFORMATION: MOR-202 VH

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser

-continued

```
            115                 120

<210> SEQ ID NO 12
<211> LENGTH: 109
<212> TYPE: PRT
<213> ORGANISM: Artificial Sequence
<220> FEATURE:
<223> OTHER INFORMATION: MOR-202 VL

<400> SEQUENCE: 12

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105

<210> SEQ ID NO 13
<211> LENGTH: 120
<212> TYPE: PRT
<213> ORGANISM: Artificial Sequence
<220> FEATURE:
<223> OTHER INFORMATION: Isatuximab VH

<400> SEQUENCE: 13

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: Isatuximab VL

<400> SEQUENCE: 14

Asp Ile Val Met Thr Gln Ser His Leu Ser Met Ser Thr Ser Leu Gly
1               5                   10                  15
```

```
Asp Pro Val Ser Ile Thr Cys Lys Ala Ser Gln Asp Val Ser Thr Val
                20                  25                  30

Val Ala Trp Tyr Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys
                100                 105

<210> SEQ ID NO 15
<211> LENGTH: 509
<212> TYPE: PRT
<213> ORGANISM: Homo sapiens

<400> SEQUENCE: 15

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Pro
                35                  40                  45

Phe Leu Trp Ala Trp Asn Ala Pro Ser Glu Phe Cys Leu Gly Lys Phe
        50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
                180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
```

|  |  |  | 275 |  |  |  | 280 |  |  |  | 285 |  |  |
|---|---|---|---|---|---|---|---|---|---|---|---|---|---|
| Ser | Lys | Ile | Pro | Asp | Ala | Lys | Ser | Pro | Leu | Pro | Val | Phe | Ala | Tyr | Thr |
|  | 290 |  |  |  |  | 295 |  |  |  |  | 300 |  |  |  |  |
| Arg | Ile | Val | Phe | Thr | Asp | Gln | Val | Leu | Lys | Phe | Leu | Ser | Gln | Asp | Glu |
| 305 |  |  |  |  | 310 |  |  |  |  | 315 |  |  |  |  | 320 |
| Leu | Val | Tyr | Thr | Phe | Gly | Glu | Thr | Val | Ala | Leu | Gly | Ala | Ser | Gly | Ile |
|  |  |  |  | 325 |  |  |  |  | 330 |  |  |  |  | 335 |  |
| Val | Ile | Trp | Gly | Thr | Leu | Ser | Ile | Met | Arg | Ser | Met | Lys | Ser | Cys | Leu |
|  |  |  | 340 |  |  |  |  | 345 |  |  |  |  | 350 |  |  |
| Leu | Leu | Asp | Asn | Tyr | Met | Glu | Thr | Ile | Leu | Asn | Pro | Tyr | Ile | Ile | Asn |
|  |  |  | 355 |  |  |  |  | 360 |  |  |  |  | 365 |  |  |
| Val | Thr | Leu | Ala | Ala | Lys | Met | Cys | Ser | Gln | Val | Leu | Cys | Gln | Glu | Gln |
|  |  | 370 |  |  |  |  | 375 |  |  |  |  | 380 |  |  |  |
| Gly | Val | Cys | Ile | Arg | Lys | Asn | Trp | Asn | Ser | Ser | Asp | Tyr | Leu | His | Leu |
| 385 |  |  |  |  | 390 |  |  |  |  | 395 |  |  |  |  | 400 |
| Asn | Pro | Asp | Asn | Phe | Ala | Ile | Gln | Leu | Glu | Lys | Gly | Gly | Lys | Phe | Thr |
|  |  |  |  | 405 |  |  |  |  | 410 |  |  |  |  | 415 |  |
| Val | Arg | Gly | Lys | Pro | Thr | Leu | Glu | Asp | Leu | Glu | Gln | Phe | Ser | Glu | Lys |
|  |  |  | 420 |  |  |  |  | 425 |  |  |  |  | 430 |  |  |
| Phe | Tyr | Cys | Ser | Cys | Tyr | Ser | Thr | Leu | Ser | Cys | Lys | Glu | Lys | Ala | Asp |
|  |  | 435 |  |  |  |  | 440 |  |  |  |  | 445 |  |  |  |
| Val | Lys | Asp | Thr | Asp | Ala | Val | Asp | Val | Cys | Ile | Ala | Asp | Gly | Val | Cys |
|  | 450 |  |  |  |  | 455 |  |  |  |  | 460 |  |  |  |  |
| Ile | Asp | Ala | Phe | Leu | Lys | Pro | Pro | Met | Glu | Thr | Glu | Glu | Pro | Gln | Ile |
| 465 |  |  |  |  | 470 |  |  |  |  | 475 |  |  |  |  | 480 |
| Phe | Tyr | Asn | Ala | Ser | Pro | Ser | Thr | Leu | Ser | Ala | Thr | Met | Phe | Ile | Val |
|  |  |  |  | 485 |  |  |  |  | 490 |  |  |  |  | 495 |  |
| Ser | Ile | Leu | Phe | Leu | Ile | Ile | Ser | Ser | Val | Ala | Ser | Leu |  |  |  |
|  |  |  | 500 |  |  |  |  | 505 |  |  |  |  |  |  |  |

CONTROL OF TRACE METALS DURING PRODUCTION OF ANTI-CD38 ANTIBODIES

CROSS-REFERENCE TO RELATED APPLICATIONS

This application claims the benefit of U.S. Provisional Application Ser. No. 62/760,782, filed 13 Nov. 2018, the entire contents of which are incorporated herein by reference.

FIELD

The disclosure relates to methods to control trace metals during production of anti-CD38 antibodies, drug substances and drug products generated using the methods, and uses of the generated drug substances and drug products.

SEQUENCE LISTING

This application contains a Sequence Listing submitted via EFS-Web, the entire content of which is incorporated herein by reference. The ASCII text file, created on 2 Nov. 2018, is named JBI6023USNP1_ST25.txt and is 91 kilobytes in size.

BACKGROUND

Over the last few decades, much research has focused on the production of recombinant proteins, e.g., monoclonal antibodies from cell culture. While media containing sera or hydrolysates has been utilized for such culture, chemically defined media were developed to minimize lot-to-lot variation of media components (Luo and Chen, *Biotechnology and Bioengineering* 97(6):1654-59, 2007). An improved understanding of cell culture has permitted a shift to chemically defined media without compromising product quality while maintaining relatively high viabilities.

N-glycosylation during production of antibodies may mediate their antigenicity, rate of clearance in vivo, stability and Fc-mediated effector functions and can be dependent on cell culture conditions. Thus, there is a need to develop methods that can provide predictable glycosylation profiles of therapeutic antibodies obtained from cell culture in chemically defined media.

BRIEF SUMMARY

The disclosure provides a method of producing an anti-CD38 antibody expressed from a polynucleotide encoding a heavy chain variable region (VH) of SEQ ID NO: 7 and a light chain variable region (VL) of SEQ ID NO: 8 having a G1F oligosaccharide content between about 15% and about 27%, comprising:
 preparing a culture medium comprising about 8.5 parts per billion (ppb) or less manganese (Mn); and
 controlling the G1F oligosaccharide content of the anti-CD38 antibody by culturing a host cell comprising the polynucleotide encoding the VH of SEQ ID NO: 7 and the VL of SEQ ID NO: 8 in the culture medium prepared in step a), thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and a VL of SEQ ID NO: 8 having a G1F oligosaccharide content between about 15% and about 27%, comprising:
 culturing a host cell expressing the polynucleotide encoding the VH of SEQ ID NO: 7 and the VL of SEQ ID NO: 8 in conditions that the anti-CD38 antibody is produced; and
 controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody having the G1F oligosaccharide content between about 15% and about 27%.

The disclosure also provides a method of producing a drug product comprising an anti-CD38 antibody expressed from a polynucleotide encoding the VH of SEQ ID NO: 7 and the VL of SEQ ID NO: 8 and having a G1F oligosaccharide content between about 15% and about 27%, comprising:
 preparing a culture medium comprising about 8.5 ppb or less Mn;
 controlling the G1F oligosaccharide content of the anti-CD38 antibody by culturing a host cell comprising the polynucleotide encoding the VH of SEQ ID NO: 7 and the VL of SEQ ID NO: 8 in the culture medium prepared in step a), thereby producing the anti-CD38 antibody having the G1F oligosaccharide content between about 15% and about 27%; and
 formulating the anti-CD38 antibody as a drug product.

DETAILED DESCRIPTION

Figure 1:
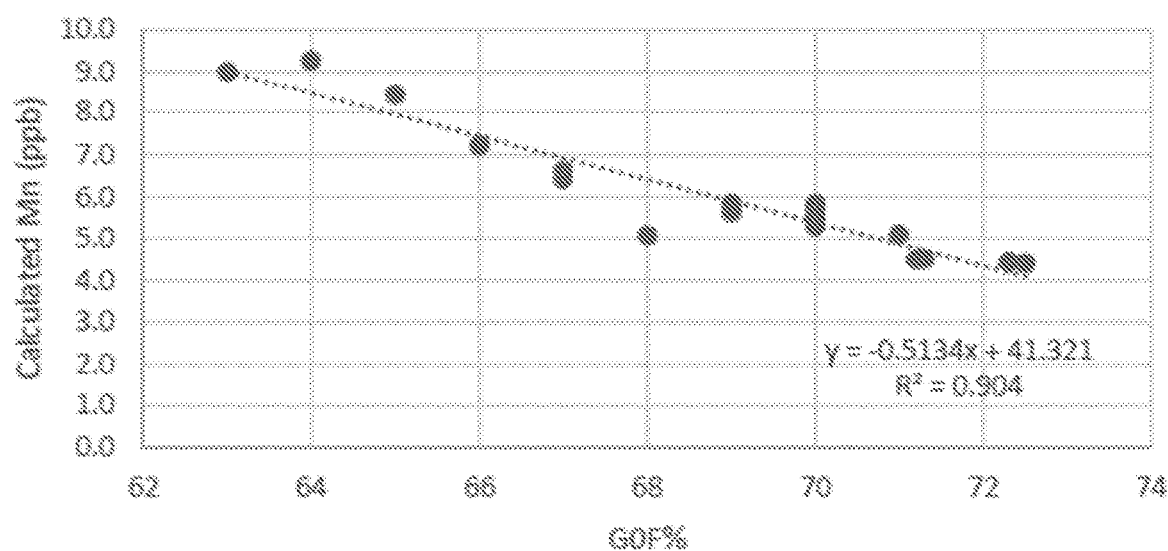
FIG. 1 shows the correlation of DARZALEX® (daratumumab) percentage of G0F oligosaccharides (G0F %) vs. dry powder medium (DPM) calculated manganese (Mn) concentration in various manufacturing batches. Y-axis: Mn concentration, parts per billion (ppb); X-axis: G0F %.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the disclosure pertains.

Although any methods and materials similar or equivalent to those described herein may be used in the practice for testing of the present disclosure, exemplary materials and methods are described herein. In describing and claiming the present disclosure, the following terminology will be used.

Definitions

As used in this specification and the appended claims, the singular forms "a," "an," and "the" include plural referents unless the content clearly dictates otherwise. Thus, for example, reference to "a cell" includes a combination of two or more cells, and the like.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Antibodies" refer to immunoglobulin molecules having two heavy chains (HC) and two light chains (LC) interconnected by disulfide bonds. Each heavy chain is comprised of a heavy chain variable region (VH) and a heavy chain constant region, the heavy chain constant region divided into regions CH1, hinge, CH2 and CH3. Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Antibodies include monoclonal antibodies including murine, human, humanized and chimeric antibodies, bispecific or multispecific antibodies. Immunoglobulins may be assigned to five major classes, IgA, IgD, IgE, IgG and IgM, depending on the heavy chain constant region amino acid sequence. IgA and IgG are further sub-classified as isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

"Antigen-binding fragment" refers to a portion of an immunoglobulin molecule that retains the antigen binding properties of the parental full-length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001; Int. Pat. Publ. No. WO1988/01649; Int. Pat. Publ. No. WO1994/13804; Int. Pat. Publ. No. WO1992/01047.

"Biosimilar" (of an approved reference product/biological drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extend the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance. The reference product may be approved in at least one of the U.S., Europe, or Japan.

"CD38" refers to cluster of differentiation 38 protein, a glycoprotein expressed on immune cells, including plasma cells, natural killer cells and sub-populations of B and T cells.

"Cell culture medium" and "culture medium" refer to a solution containing components or nutrients which nourish growing mammalian cells. Typically, the nutrients include essential and non-essential amino acids, vitamins, energy sources, lipids, and trace elements required by the cell for minimal growth and/or survival. Such a solution may also contain further nutrients or supplementary components that enhance growth and/or survival above the minimal rate, including, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) *J Exp Med* 132: 211-50) (Kabat et al., *Sequences of Proteins of Immunological Interest*, 5th Ed. Public Health Service, National Institutes of Health, Bethesda, Md., 1991), Chothia (Chothia et al., *J Mol Biol* 196: 901-17, 1987), IMGT (Lefranc et al., *Dev Comp Immunol* 27: 55-77, 2003) and AbM (Martin and Thornton, *J Bmol Biol* 263: 800-15, 1996). The correspondence between the various delineations and variable region numbering are described (see e.g. Lefranc et al., *Dev Comp Immunol* 27: 55-77, 2003; Honegger and Pluckthun, *J Mol Biol* 309:657-70, 2001; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed disclosure. Embodiments described in terms of the phrase "comprising" (or its equivalents) also provide as embodiments those independently described in terms of "consisting of" and "consisting essentially of."

"Culture", "culturing", "cultured", and "cell culture" refer to a population of cells that is suspended in a culture medium under conditions suitable to survival and/or growth of the cell population. Cell culture includes fed-batch cell culture and perfusion cell culture.

"Drug substance" or "DS" refers to any substance or mixture of substances intended to be used in the manufacture of a drug (medicinal) product and that, when used in the production of a drug, becomes an active ingredient of the drug product. Such substances are intended to furnish pharmacological activity or other direct effect in the diagnosis, cure, mitigation, treatment, or prevention of disease or to affect the structure or function of the body.

"Drug product" or "DP" refers to a finished dosage form, for example, a tablet, capsule or solution that contains an active pharmaceutical ingredient (e.g., drug substance), generally, but not necessarily, in association with inactive ingredients.

"Expression vector" refers to a vector that can be utilized in a biological system or in a reconstituted biological system to direct the translation of a polypeptide encoded by a polynucleotide sequence present in the expression vector.

"G0F" refers to an asialo, agalacto core-fucosylated biantennary glycan.

"G0F oligosaccharide content" refers to a percentage of G0F oligosaccharides (G0F %) in a glycoprotein oligosaccharide.

"G1F" refers to an asialo, mono-galacto core-fucosylated biantennary glycan.

"G1F oligosaccharide content" refers to a percentage of G1F oligosaccharides (G1F %) in a glycoprotein oligosaccharide.

"G2F" refers to an asialo, di-galacto core-fucosylated biantennary glycan.

"G2F oligosaccharide content" refers to a percentage of G2F oligosaccharides (G2F %) in a glycoprotein oligosaccharide "GMP-compliant conditions" refers to manufacturing under good manufacturing practice (CGMP) regulations enforced by the Food and Drug Administration (FDA). CGMPs provide for systems that assure proper design, monitoring, and control of manufacturing processes and facilities. Adherence to the CGMP regulations assures the identity, strength, quality, and purity of drug products by requiring that manufacturers of medications adequately control manufacturing operations. This includes establishing strong quality management systems, obtaining appropriate quality raw materials, establishing robust operating procedures, detecting and investigating product quality deviations, and maintaining reliable testing laboratories. This formal system of controls at a pharmaceutical company, if adequately put into practice, helps to prevent instances of contamination, mix-ups, deviations, failures, and errors. This assures that drug products meet their quality standards.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., *J Mol Biol* 296:57-86, 2000, or synthetic HCDR3 incorporated into human immunoglobulin gene libraries displayed on phage, for example as described in Shi et al., *J Mol Biol* 397:385-96, 2010, and in Int. Pat. Publ. No. WO2009/085462. Antibodies in which at least one CDR is derived from a non-human species are not included in the definition of "human antibody".

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Label" and "labeling" are used interchangeably herein and refers to all labels and displays of written, printed, or graphic information on, in or accompanying a container or package comprising a drug, such as daratumumab, or otherwise available electronically or on internet. "Label" and "labeling" include package insert and prescribing information.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. Monoclonal antibodies may have heterogeneous glycosylation within the antibody population. Monoclonal antibody may be monospecific or multispecific such as bispecific, monovalent, bivalent or multivalent.

"Polynucleotide" refers to a synthetic molecule comprising a chain of nucleotides covalently linked by a sugar-phosphate backbone or other equivalent covalent chemistry. cDNA is a typical example of a polynucleotide.

"ppb" or "parts per billion" refers to an amount of metal in a solution or solid. When measured in solution, ppb equals to µg/L concentration of the metal in the solution. When measured in solids, ppb equals to µg/kg concentration of the metal in the solution.

"Recombinant" refers to polynucleotides, antibodies and other proteins that are prepared, expressed, created or isolated by recombinant means when segments from different sources are joined to produce recombinant DNA, antibodies or proteins. "Recombinant antibody" includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

"Reference product" refers to an approved biological product against which a biosimilar product is compared. A reference product is approved based on, among other things, a full complement of safety and effectiveness data and is approved in at least one of the U.S., Europe, or Japan.

"Refractory" refers to a disease that does not respond to a treatment. A refractory disease can be resistant to a treatment before or at the beginning of the treatment, or a refractory disease can become resistant during a treatment.

"Relapsed" refers to the return of a disease or the signs and symptoms of a disease after a period of improvement after prior treatment with a therapeutic.

"Specific binding" or "specifically binds" or "binds" refer to an antibody binding to an antigen or an epitope within the antigen with greater affinity than for other antigens. Typically, the antibody binds to the antigen or the epitope within the antigen with an equilibrium dissociation constant ($K_D$) of about $1\times10^{-8}$ M or less, for example about $1\times10^{-9}$ M or less, about $1\times10^{10}$ M or less, about $1\times10^{11}$ M or less, or about $1\times10^{12}$ M or less, typically with the $K_D$ that is at least one hundred fold less than its $K_D$ for binding to a non-specific antigen (e.g., BSA, casein). The dissociation constant may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset).

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Treat" or "treatment" refers to both therapeutic treatment and prophylactic or preventative measures, wherein the object is to prevent or slow down (lessen) an undesired physiological change or disorder, such as complications due to cancer. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder as well as those prone to have the condition or disorder or those in which the condition or disorder is to be prevented.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

Methods of the Disclosure

The disclosure provides a method of producing an anti-CD38 antibody expressed from a polynucleotide encoding a heavy chain variable region (VH) of SEQ ID NO: 7 and a light chain variable region (VL) of SEQ ID NO 8 having a G1F oligosaccharide content between about 15% and about 27%, comprising:

preparing a culture medium comprising about 8.5 parts per billion (ppb) or less manganese (Mn); and controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:

preparing a culture medium comprising about 8.5 ppb or less Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, comprising:

preparing a culture medium comprising about 8.5 ppb or less Mn; and controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:

preparing a culture medium comprising about 8.5 ppb or less Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

In some embodiments, the G1F oligosaccharide content of the anti-CD38 antibody is between about 15% and about 25%.

In some embodiments, the G1F oligosaccharide content of the anti-CD38 antibody is between about 21% and about 25%.

In some embodiments, a G0F oligosaccharide content of the anti-CD38 antibody is between about 65% and about 74%.

In some embodiments, the G0F oligosaccharide content of the anti-CD38 antibody is between about 68% and 74%.

In some embodiments, preparing the culture medium comprises measuring Mn concentration in one or more batches of raw material components used to prepare the culture medium and selecting those one or more batches of raw material components that in combination contain about 8.5 ppb or less Mn.

In some embodiments, the culture medium is prepared to comprise between about 4.0 ppb and about 8.5 ppb Mn.

In some embodiments, the culture medium is prepared to comprise between about 4.0 ppb and about 6.5 ppb Mn.

In some embodiments, the culture medium is prepared to comprise between about 5.0 ppb and about 6.5 ppb Mn.

In some embodiments, the G1F oligosaccharide content of the anti-CD38 antibody is between about 15% and about 27%, the G0F oligosaccharide content of the anti-CD38 antibody is between about 65% and about 74%, and the culture medium is prepared to comprise between about 4.0 ppb and about 8.5 ppb Mn.

In some embodiments, the G1F oligosaccharide content of the anti-CD38 antibody is between about 15% and about 25%, the G0F oligosaccharide content of the anti-CD38 antibody is between about 68% and about 74%, and the culture medium is prepared to comprise between about 4.0 ppb and about 6.5 ppb Mn.

In some embodiments, the G1F oligosaccharide content of the anti-CD38 antibody is between about 21% and about 25%, the G0F oligosaccharide content of the anti-CD38 antibody is between about 68% and about 74%, and the culture medium is prepared to comprise between about 5.0 ppb and about 6.5 ppb Mn.

In some embodiments, the anti-CD38 antibody expressed from the polynucleotide encoding the VH of SEQ ID NO: 7 and the VL of SEQ ID NO: 8 comprises the VH of SEQ ID NO: 7 and the VL of SEQ ID NO: 8.

In some embodiments, the culture medium is a basal medium or a feed medium.

In some embodiments, the culturing comprises a fed-batch culture or a perfusion culture.

In some embodiments, the host cell is an eukaryotic cell.

In some embodiments, the eukaryotic cell is a CHO cell, a PER.C6 cell, a NS0 cell, a Sp2/0 cell or a BHK cell.

In some embodiments, the CHO cell is a CHO-K1 cell, a CHO-DG44 cell, a CHO-S cell or a CHO-DXB11 cell.

In some embodiments, the CHO cell is deficient in glutamine synthetase (GS).

In some embodiments, the method is conducted under GMP-compliant conditions.

In some embodiments, the anti-CD38 antibody comprises the VH of SEQ ID NO: 7 and the VL of SEQ ID NO: 9.

In some embodiments, the anti-CD38 antibody comprises an IgG1 isotype.

In some embodiments, the anti-CD38 antibody comprises a heavy chain (HC) of SEQ ID NO: 9 and a light chain (LC) of SEQ ID NO: 10.

In some embodiments, the anti-CD38 antibody is a biosimilar.

In some embodiments, the anti-CD38 antibody is a biosimilar or DARZALEX® (daratumumab).

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, comprising:
preparing a culture medium comprising between about 4.0 ppb and about 8.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 and having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, comprising:
preparing a culture medium comprising between about 4.0 ppb and about 8.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, comprising:
preparing a culture medium comprising between about 4.0 ppb and about 8.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:
preparing a culture medium comprising between about 4.0 ppb and about 8.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:
preparing a culture medium comprising between about 4.0 ppb and about 6.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25%.

The disclosure also provides a method of producing an anti-CD38 antibody comprising the VH of SEQ ID NO: 7 and the VL of SEQ ID NO: 8 having a G1F oligosaccharide content between about 15% and about 25%, and a G0F oligosaccharide content between about 68% and about 74%, comprising:
preparing a culture medium comprising between about 4.0 ppb and about 6.5 ppb Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, comprising:
preparing a culture medium comprising between about 5.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:
preparing a culture medium comprising between about 5.0 ppb and about 6.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 21% and about 25%, comprising:
preparing a culture medium comprising between about 5.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25%.

The disclosure also provides a method of producing an anti-CD38 antibody comprising the VH of SEQ ID NO: 7 and the VL of SEQ ID NO: 8 having a G1F oligosaccharide content between about 21% and about 25%, and a G0F oligosaccharide content between about 68% and about 74%, comprising:
preparing a culture medium comprising between about 5.0 ppb and about 6.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25% and the G0F oligosaccharide content between about 66% and about 74%.

The disclosure provides a method of producing an anti-CD38 antibody expressed from a polynucleotide encoding the VH of SEQ ID NO: 7 and the VL of SEQ ID NO: 8 having a G1F oligosaccharide content between about 15% and about 27%, wherein the anti-CD38 antibody is an IgG1 isotype, comprising:
preparing a culture medium comprising about 8.5 ppb or less Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 and having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:
preparing a culture medium comprising about 8.5 ppb or less Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure provides a method of producing an anti-CD38 antibody comprising the VH of SEQ ID NO: 7 and the VL of SEQ ID NO: 8 and having a G1F oligosaccharide content between about 15% and about 27%, wherein the anti-CD38 antibody is an IgG1 isotype, comprising:
preparing a culture medium comprising about 8.5 ppb or less Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 and having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising about 8.5 ppb or less Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 and having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, wherein the anti-CD38 antibody is an IgG1 isotype, comprising:

preparing a culture medium comprising between about 4.0 ppb and about 8.5 ppb Mn; and controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising between about 4.0 ppb and about 8.5 ppb Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, wherein the anti-CD38 antibody is an IgG1 isotype, comprising:

preparing a culture medium comprising between about 4.0 ppb and about 8.5 ppb Mn; and controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising between about 4.0 ppb and about 8.5 ppb Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 25%, wherein the anti-CD38 antibody is an IgG1 isotype, comprising:

preparing a culture medium comprising between about 4.0 ppb and about 6.5 ppb Mn; and controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 25%, and a G0F oligosaccharide content between about 68% and about 74%, wherein the anti-CD38 antibody is an IgG1 isotype, comprising:

preparing a culture medium comprising between about 4.0 ppb and about 6.5 ppb Mn; and controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 15% and about 25%, wherein the anti-CD38 antibody is an IgG1 isotype, comprising:
preparing a culture medium comprising between about 4.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25%.

The disclosure also provides a method of producing an anti-CD38 antibody comprising the VH of SEQ ID NO: 7 and the VL of SEQ ID NO: 8 having a G1F oligosaccharide content between about 15% and about 25%, and a G0F oligosaccharide content between about 68% and about 74%, wherein the anti-CD38 antibody is an IgG1 isotype, comprising:
preparing a culture medium comprising between about 4.0 ppb and about 6.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 21% and about 25%, wherein the anti-CD38 antibody is an IgG1 isotype, comprising:
preparing a culture medium comprising between about 5.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 21% and about 25%, and a G0F oligosaccharide content between about 68% and about 74%, wherein the anti-CD38 antibody is an IgG1 isotype, comprising:
preparing a culture medium comprising between about 5.0 ppb and about 6.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 21% and about 25%, wherein the anti-CD38 antibody is an IgG1 isotype, comprising:
preparing a culture medium comprising between about 5.0 ppb and about 6.5 ppb Mn; and
controlling the G1F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25%.

The disclosure also provides a method of producing an anti-CD38 antibody comprising the VH of SEQ ID NO: 7 and the VL of SEQ ID NO: 8 having a G1F oligosaccharide content between about 21% and about 25%, and a G0F oligosaccharide content between about 68% and about 74%, wherein the anti-CD38 antibody is an IgG1 isotype, comprising:
preparing a culture medium comprising between about 5.0 ppb and about 6.5 ppb Mn; and
controlling the G1F oligosaccharide content and the G0F oligosaccharide content of the anti-CD38 antibody by culturing a host cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25% and the G0F oligosaccharide content between about 66% and about 74%.

The disclosure provides a method of producing an anti-CD38 antibody expressed from a polynucleotide encoding a heavy chain (HC) of SEQ ID NO: 9 and a light chain (LC) of SEQ ID NO: 10 having a G1F oligosaccharide content between about 15% and about 27%, comprising:
preparing a culture medium comprising about 8.5 ppb or less Mn; and
controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising about 8.5 ppb or less Mn; and
controlling the G1F oligosaccharide content and the G0F oligosaccharide content of the anti-CD38 antibody by culturing a host cell comprising the polynucleotide encoding the HC of SEQ ID NO: 9 and the LC of SEQ ID NO: 10 in the culture medium comprising about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%.

The disclosure provides a method of producing an anti-CD38 antibody comprising the HC of SEQ ID NO: 9 and the LC of SEQ ID NO: 10 having a G1F oligosaccharide content between about 15% and about 27%, comprising:
preparing a culture medium comprising about 8.5 ppb or less Mn; and
controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising about 8.5 ppb or less Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising about 8.5 ppb or less Mn; and
controlling the G1F oligosaccharide content and the G0F oligosaccharide content of the anti-CD38 antibody by culturing a host cell comprising the polynucleotide encoding the HC of SEQ ID NO: 9 and the LC of SEQ ID NO: 10 in the culture medium comprising about 8.5 ppb or less Mn, thereby producing the anti-CD38 antibody comprising the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, comprising:
preparing a culture medium comprising between about 4.0 ppb and about 8.5 ppb Mn; and
controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising between about 4.0 ppb and about 8.5 ppb Mn; and
controlling the G1F oligosaccharide content and the G0F oligosaccharide content of the anti-CD38 antibody by culturing a host cell comprising the polynucleotide the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 and having the G1F oligosaccharide content between about 15% and about 27% and the G0F oligosaccharide content between about 65% and about 74%.

The disclosure also provides a method of producing an anti-CD38 antibody comprising the HC of SEQ ID NO: 9 and the LC of SEQ ID NO: 10 having a G1F oligosaccharide content between about 15% and about 27%, comprising:
preparing a culture medium comprising between about 4.0 ppb and about 8.5 ppb Mn; and
controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising between about 4.0 ppb and about 8.5 ppb Mn; and
controlling the G1F oligosaccharide content and the G0F oligosaccharide content of the anti-CD38 antibody by culturing a host cell comprising the polynucleotide the HC of SEQ ID NO: 9 and the LC of SEQ ID NO: 10 in the culture medium comprising between about 4.0 ppb and about 8.5 ppb Mn, thereby producing the anti-CD38 antibody comprising the HC of SEQ ID NO: 9 and the LC of SEQ ID NO: 10 and having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, and a G0F oligosaccharide content between about 68% and about 74%, comprising:
  preparing a culture medium comprising between about 4.0 ppb and about 6.5 ppb Mn; and
  controlling the G1F oligosaccharide content and the G0F oligosaccharide content of the anti-CD38 antibody by culturing a host cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 66% and about 74%.

The disclosure also provides a method of producing an anti-CD38 antibody comprising the HC of SEQ ID NO: 9 and the LC of SEQ ID NO: 10 having a G1F oligosaccharide content between about 15% and about 25%, comprising:
  preparing a culture medium comprising between about 4.0 ppb and about 6.5 ppb Mn; and
  controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25%.

The disclosure also provides a method of producing an anti-CD38 antibody comprising the HC of SEQ ID NO: 9 and the LC of SEQ ID NO: 10 having a G1F oligosaccharide content between about 15% and about 25%, and a G0F oligosaccharide content between about 68% and about 74%, comprising:
  preparing a culture medium comprising between about 4.0 ppb and about 6.5 ppb Mn; and
  controlling the G1F oligosaccharide content and the G0F oligosaccharide content of the anti-CD38 antibody by culturing a host cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25% and the G0F oligosaccharide content between about 66% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, comprising:
  preparing a culture medium comprising between about 5.0 ppb and about 6.5 ppb Mn; and
  controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, and a G0F oligosaccharide content between about 68% and about 74%, comprising:
  preparing a culture medium comprising between about 5.0 ppb and about 6.5 ppb Mn; and
  controlling the G1F oligosaccharide content and the G0F oligosaccharide content of the anti-CD38 antibody by culturing a host cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 66% and about 74%.

The disclosure also provides a method of producing an anti-CD38 antibody comprising the HC of SEQ ID NO: 9 and the LC of SEQ ID NO: 10 having a G1F oligosaccharide content between about 21% and about 25%, comprising:
  preparing a culture medium comprising between about 5.0 ppb and about 6.5 ppb Mn; and
  controlling the G1F oligosaccharide content of the anti-CD38 antibody by culturing a host cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody comprising the HC of SEQ ID NO: 9 and the LC of SEQ ID NO: 10 having the G1F oligosaccharide content between about 21% and about 25%.

The disclosure also provides a method of producing an anti-CD38 antibody comprising the HC of SEQ ID NO: 9 and the LC of SEQ ID NO: 10 having a G1F oligosaccharide content between about 21% and about 25%, and a G0F oligosaccharide content between about 68% and about 74%, comprising:
  preparing a culture medium comprising between about 5.0 ppb and about 6.5 ppb Mn; and
  controlling the G1F oligosaccharide content and the G0F oligosaccharide content of the anti-CD38 antibody by culturing a host cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody comprising HC of SEQ ID NO: 9 and the LC of SEQ ID NO: 10 having the G1F oligosaccharide content between about 21% and about 25% and the G0F oligosaccharide content between about 66% and about 74%.

The disclosure provides a method of producing an anti-CD38 antibody expressed from a polynucleotide encoding a heavy chain variable region (VH) of SEQ ID NO: 7 and a light chain variable region (VL) of SEQ ID NO 8 having a G1F oligosaccharide content between about 15% and about 27%, comprising:

preparing a culture medium comprising about 8.5 parts per billion (ppb) or less manganese (Mn); and controlling the G1F oligosaccharide content of the anti-CD38 antibody by culturing a chinese hamster ovary (CHO) cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:

preparing a culture medium comprising about 8.5 ppb or less Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure provides a method of producing an anti-CD38 antibody comprising the VH of SEQ ID NO: 7 and the VL of SEQ ID NO: 8 having a G1F oligosaccharide content between about 15% and about 27%, comprising:

preparing a culture medium comprising about 8.5 ppb or less Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:

preparing a culture medium comprising about 8.5 ppb or less Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, comprising:

preparing a culture medium comprising between about 4.0 ppb and about 8.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 and having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, comprising:

preparing a culture medium comprising between about 4.0 ppb and about 8.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, comprising:

preparing a culture medium comprising between about 4.0 ppb and about 8.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:

preparing a culture medium comprising between about 4.0 ppb and about 8.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:
preparing a culture medium comprising between about 4.0 ppb and about 6.5 ppb Mn; and
controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25%.

The disclosure also provides a method of producing an anti-CD38 antibody comprising the VH of SEQ ID NO: 7 and the VL of SEQ ID NO: 8 having a G1F oligosaccharide content between about 15% and about 25%, and a G0F oligosaccharide content between about 68% and about 74%, comprising:
preparing a culture medium comprising between about 4.0 ppb and about 6.5 ppb Mn; and
controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, comprising:
preparing a culture medium comprising between about 5.0 ppb and about 6.5 ppb Mn; and
controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:
preparing a culture medium comprising between about 5.0 ppb and about 6.5 ppb Mn; and
controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 21% and about 25%, comprising:
preparing a culture medium comprising between about 5.0 ppb and about 6.5 ppb Mn; and
controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25%.

The disclosure also provides a method of producing an anti-CD38 antibody comprising the VH of SEQ ID NO: 7 and the VL of SEQ ID NO: 8 having a G1F oligosaccharide content between about 21% and about 25%, and a G0F oligosaccharide content between about 68% and about 74%, comprising:

preparing a culture medium comprising between about 5.0 ppb and about 6.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25% and the G0F oligosaccharide content between about 66% and about 74%.

The disclosure provides a method of producing an anti-CD38 antibody expressed from a polynucleotide encoding the VH of SEQ ID NO: 7 and the VL of SEQ ID NO: 8 having a G1F oligosaccharide content between about 15% and about 27%, wherein the anti-CD38 antibody is an IgG1 isotype, comprising:

preparing a culture medium comprising about 8.5 ppb or less Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 and having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising about 8.5 ppb or less Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure provides a method of producing an anti-CD38 antibody comprising the VH of SEQ ID NO: 7 and the VL of SEQ ID NO: 8 and having a G1F oligosaccharide content between about 15% and about 27%, wherein the anti-CD38 antibody is an IgG1 isotype, comprising:

preparing a culture medium comprising about 8.5 ppb or less Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 and having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising about 8.5 ppb or less Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody comprising the VH of SEQ ID NO: 7 and the VL of SEQ ID NO: 8 and having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, wherein the anti-CD38 antibody is an IgG1 isotype, comprising:

preparing a culture medium comprising between about 4.0 ppb and about 8.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising between about 4.0 ppb and about 8.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, wherein the anti-CD38 antibody is an IgG1 isotype, comprising:

preparing a culture medium comprising between about 4.0 ppb and about 8.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, wherein the anti-CD38 antibody is an IgG1 isotype, comprising:

preparing a culture medium comprising between about 4.0 ppb and about 8.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 25%, wherein the anti-CD38 antibody is an IgG1 isotype, comprising:

preparing a culture medium comprising between about 4.0 ppb and about 6.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 25%, and a G0F oligosaccharide content between about 68% and about 74%, wherein the anti-CD38 antibody is an IgG1 isotype, comprising:

preparing a culture medium comprising between about 4.0 ppb and about 6.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 15% and about 25%, wherein the anti-CD38 antibody is an IgG1 isotype, comprising:

preparing a culture medium comprising between about 4.0 ppb and about 6.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25%.

The disclosure also provides a method of producing an anti-CD38 antibody comprising the VH of SEQ ID NO: 7 and the VL of SEQ ID NO: 8 having a G1F oligosaccharide content between about 15% and about 25%, and a G0F oligosaccharide content between about 68% and about 74%, wherein the anti-CD38 antibody is an IgG1 isotype, comprising:

preparing a culture medium comprising between about 4.0 ppb and about 6.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25% and the G0F oligosaccharide content between about 66% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 21% and about 25%, wherein the anti-CD38 antibody is an IgG1 isotype, comprising:

preparing a culture medium comprising between about 5.0 ppb and about 6.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 21% and about 25%, and a G0F oligosaccharide content between about 68% and about 74%, wherein the anti-CD38 antibody is an IgG1 isotype, comprising:

preparing a culture medium comprising between about 5.0 ppb and about 6.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 66% and about 74%.

The disclosure also provides a method of producing an anti-CD38 antibody comprising the VH of SEQ ID NO: 7 and the VL of SEQ ID NO: 8 having a G1F oligosaccharide content between about 21% and about 25%, wherein the anti-CD38 antibody is an IgG1 isotype, comprising:

preparing a culture medium comprising between about 5.0 ppb and about 6.5 ppb Mn; and controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25%.

The disclosure also provides a method of producing an anti-CD38 antibody comprising the VH of SEQ ID NO: 7 and the VL of SEQ ID NO: 8 having a G1F oligosaccharide content between about 21% and about 25%, and a G0F oligosaccharide content between about 68% and about 74%, wherein the anti-CD38 antibody is an IgG1 isotype, comprising:

preparing a culture medium comprising between about 5.0 ppb and about 6.5 ppb Mn; and controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed the VH of SEQ ID NO: 7 and the VL of SEQ ID NO: 8 having the G1F oligosaccharide content between about 21% and about 25% and the G0F oligosaccharide content between about 66% and about 74%.

The disclosure provides a method of producing an anti-CD38 antibody expressed from a polynucleotide encoding a heavy chain (HC) of SEQ ID NO: 9 and a light chain (LC) of SEQ ID NO: 10 having a G1F oligosaccharide content between about 15% and about 27%, comprising:

preparing a culture medium comprising about 8.5 ppb or less Mn; and controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:

preparing a culture medium comprising about 8.5 ppb or less Mn; and controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%.

The disclosure provides a method of producing an anti-CD38 antibody comprising the HC of SEQ ID NO: 9 and the LC of SEQ ID NO: 10 having a G1F oligosaccharide content between about 15% and about 27%, comprising:

preparing a culture medium comprising about 8.5 ppb or less Mn; and controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising about 8.5 ppb or less Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:

preparing a culture medium comprising about 8.5 ppb or less Mn; and controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising about 8.5 ppb or less Mn, thereby producing the anti-CD38 antibody comprising the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, comprising:

preparing a culture medium comprising between about 4.0 ppb and about 8.5 ppb Mn; and controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising between about 4.0 ppb and about 8.5 ppb Mn; and
controlling the G1F oligosaccharide content and the G0F oligosaccharide content of the anti-CD38 antibody by culturing a CHO cell comprising the polynucleotide the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 and having the G1F oligosaccharide content between about 15% and about 27% and the G0F oligosaccharide content between about 65% and about 74%.

The disclosure also provides a method of producing an anti-CD38 antibody comprising the HC of SEQ ID NO: 9 and the LC of SEQ ID NO: 10 having a G1F oligosaccharide content between about 15% and about 27%, comprising:
preparing a culture medium comprising between about 4.0 ppb and about 8.5 ppb Mn; and
controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising between about 4.0 ppb and about 8.5 ppb Mn; and
controlling the G1F oligosaccharide content and the G0F oligosaccharide content of the anti-CD38 antibody by culturing a CHO cell comprising the polynucleotide the HC of SEQ ID NO: 9 and the LC of SEQ ID NO: 10 in the culture medium comprising between about 4.0 ppb and about 8.5 ppb Mn, thereby producing the anti-CD38 antibody comprising the HC of SEQ ID NO: 9 and the LC of SEQ ID NO: 10 and having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, and a G0F oligosaccharide content between about 68% and about 74%, comprising:
preparing a culture medium comprising between about 4.0 ppb and about 6.5 ppb Mn; and
controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 66% and about 74%.

The disclosure also provides a method of producing an anti-CD38 antibody comprising the HC of SEQ ID NO: 9 and the LC of SEQ ID NO: 10 having a G1F oligosaccharide content between about 15% and about 25%, comprising:
preparing a culture medium comprising between about 4.0 ppb and about 6.5 ppb Mn; and
controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25%.

The disclosure also provides a method of producing an anti-CD38 antibody comprising the HC of SEQ ID NO: 9 and the LC of SEQ ID NO: 10 having a G1F oligosaccharide content between about 15% and about 25%, and a G0F oligosaccharide content between about 68% and about 74%, comprising:
preparing a culture medium comprising between about 4.0 ppb and about 6.5 ppb Mn; and
controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25% and the G0F oligosaccharide content between about 66% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, comprising:
preparing a culture medium comprising between about 5.0 ppb and about 6.5 ppb Mn; and
controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, and a G0F oligosaccharide content between about 68% and about 74%, comprising:

preparing a culture medium comprising between about 5.0 ppb and about 6.5 ppb Mn; and controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 66% and about 74%.

The disclosure also provides a method of producing an anti-CD38 antibody comprising the HC of SEQ ID NO: 9 and the LC of SEQ ID NO: 10 having a G1F oligosaccharide content between about 21% and about 25%, comprising:

preparing a culture medium comprising between about 5.0 ppb and about 6.5 ppb Mn; and controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody comprising the HC of SEQ ID NO: 9 and the LC of SEQ ID NO: 10 having the G1F oligosaccharide content between about 21% and about 25%.

The disclosure also provides a method of producing an anti-CD38 antibody comprising the HC of SEQ ID NO: 9 and the LC of SEQ ID NO: 10 having a G1F oligosaccharide content between about 21% and about 25%, and a G0F oligosaccharide content between about 68% and about 74%, comprising:

preparing a culture medium comprising between about 5.0 ppb and about 6.5 ppb Mn; and controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody comprising HC of SEQ ID NO: 9 and the LC of SEQ ID NO: 10 having the G1F oligosaccharide content between about 21% and about 25% and the G0F oligosaccharide content between about 66% and about 74%.

The disclosure also provides a method of producing an anti-CD38 antibody expressed from a polynucleotide encoding the VH of SEQ ID NO: 7 and a VL of SEQ ID NO: 8 having a G1F oligosaccharide content between about 15% and about 27%, comprising:

culturing a host cell expressing the polynucleotide encoding the VH of SEQ ID NO: 7 and the VL of SEQ ID NO: 8 in conditions that the anti-CD38 antibody is produced; and controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody having the G1F oligosaccharide content between about 15% and about 27%.

In some embodiments, the G1F oligosaccharide content of the anti-CD38 antibody is between about 15% and about 25%.

In some embodiments, the G1F oligosaccharide content of the anti-CD38 antibody is between about 21% and about 25%.

In some embodiments, a G0F oligosaccharide content of the anti-CD38 antibody is between about 65% and about 74%.

In some embodiments, the G0F oligosaccharide content of the anti-CD38 antibody is between about 68% and 74%.

In some embodiments, the concentration of Mn in the culture medium is regulated to comprise between about 4.0 ppb and about 8.5 ppb Mn.

In some embodiments, the concentration of Mn in the culture medium is regulated to comprise between about 4.0 ppb and about 6.5 ppb Mn.

In some embodiments, the concentration of Mn in the culture medium is regulated to comprise between about 5.0 ppb and about 6.5 ppb Mn.

In some embodiments, the G1F oligosaccharide content of the anti-CD38 antibody is between about 15% and about 27%, the G0F oligosaccharide content of the anti-CD38 antibody is between about 65% and about 74%, and the culture medium is regulated to comprise between about 4.0 ppb and about 8.5 ppb Mn.

In some embodiments, the G1F oligosaccharide content of the anti-CD38 antibody is between about 15% and about 25%, the G0F oligosaccharide content of the anti-CD38 antibody is between about 68% and about 74%, and the culture medium is regulated to comprise between about 4.0 ppb and about 6.5 ppb Mn.

In some embodiments, the G1F oligosaccharide content of the anti-CD38 antibody is between about 21% and about 25%, the G0F oligosaccharide content of the anti-CD38 antibody is between about 68% and about 74%, and the culture medium is regulated to comprise between about 5.0 ppb and about 6.5 ppb Mn.

In some embodiments, the culture medium is a basal medium or a feed medium.

In some embodiments, culturing comprises a fed-batch culture or a perfusion culture.

In some embodiments, the host cell is an eukaryotic cell.

In some embodiments, the eukaryotic cell is a CHO cell, a PER.C6 cell, a NS0 cell, a Sp2/0 cell or a BHK cell.

In some embodiments, the CHO cell is a CHO-K1 cell, a CHO-DG44 cell, a CHO-S cell or a CHO-DXB11 cell.

In some embodiments, the CHO cell is deficient in GS.

In some embodiments, the method is conducted under GMP-compliant conditions.

In some embodiments, the anti-CD38 antibody comprises the VH of SEQ ID NO: 7 and the VL of SEQ ID NO: 9.

In some embodiments, the anti-CD38 antibody comprises an IgG1 isotype.

In some embodiments, the anti-CD38 antibody comprises the HC of SEQ ID NO: 9 and the LC of SEQ ID NO: 10.

In some embodiments, the anti-CD38 antibody is a biosimilar.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, comprising:
- culturing a host cell expressing the polynucleotide encoding the VH of SEQ ID NO: 7 and the VL of SEQ ID NO: 8 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:
- culturing a host cell expressing the polynucleotide encoding the VH of SEQ ID NO: 7 and the VL of SEQ ID NO: 8 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the VH of SEQ ID NO: 7 and the VL of SEQ ID NO: 8 having the G1F oligosaccharide content between about 15% and about 27% and the G0F oligosaccharide content between about 65% and about 74%.

The disclosure provides a method of producing an anti-CD38 antibody comprising the VH of SEQ ID NO: 7 and the VL of SEQ ID NO: 8 having a G1F oligosaccharide content between about 15% and about 27%, comprising:
- culturing a host cell expressing the polynucleotide encoding the VH of SEQ ID NO: 7 and the VL of SEQ ID NO: 8 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:
- culturing a host cell expressing the polynucleotide encoding the VH of SEQ ID NO: 7 and the VL of SEQ ID NO: 8 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, comprising:
- culturing a host cell expressing the polynucleotide encoding the VH of SEQ ID NO: 7 and the VL of SEQ ID NO: 8 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, comprising:
- culturing a host cell expressing the polynucleotide encoding the VH of SEQ ID NO: 7 and the VL of SEQ ID NO: 8 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the VH of SEQ ID NO: 7 and the VL of SEQ ID NO:

8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, comprising:
culturing a host cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:
culturing a host cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, comprising:
culturing a host cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:
culturing a host cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 68% and about 74%.

The disclosure also provides a method of producing an anti-CD38 antibody comprising the VH of SEQ ID NO: 7 and the VL of SEQ ID NO: 8 having a G1F oligosaccharide content between about 15% and about 25%, comprising:
culturing a host cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25%.

The disclosure also provides a method of producing an anti-CD38 antibody comprising the VH of SEQ ID NO: 7 and the VL of SEQ ID NO: 8 having a G1F oligosaccharide content between about 15% and about 25%, and a G0F oligosaccharide content between about 68% and about 74%, comprising:
culturing a host cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25% and the G0F oligosaccharide content between about 68% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, comprising:
  culturing a host cell expressing the polynucleotide encoding the VH of SEQ ID NO: 7 and the VL of SEQ ID NO: 8 in conditions that the anti-CD38 antibody is produced; and
  controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:
  culturing a host cell expressing the polynucleotide encoding the VH of SEQ ID NO: 7 and the VL of SEQ ID NO: 8 in conditions that the anti-CD38 antibody is produced; and
  controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 68% and about 74%.

The disclosure also provides a method of producing an anti-CD38 antibody comprising the VH of SEQ ID NO: 7 and the VL of SEQ ID NO: 8 having a G1F oligosaccharide content between about 21% and about 25%, comprising:
  culturing a host cell expressing the polynucleotide encoding the VH of SEQ ID NO: 7 and the VL of SEQ ID NO: 8 in conditions that the anti-CD38 antibody is produced; and
  controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25%.

The disclosure also provides a method of producing an anti-CD38 antibody comprising the VH of SEQ ID NO: 7 and the VL of SEQ ID NO: 8 having a G1F oligosaccharide content between about 21% and about 25%, and a G0F oligosaccharide content between about 68% and about 74%, comprising:
  culturing a host cell expressing the polynucleotide encoding the VH of SEQ ID NO: 7 and the VL of SEQ ID NO: 8 in conditions that the anti-CD38 antibody is produced; and
  controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25% and the G0F oligosaccharide content between about 68% and about 74%.

The disclosure provides a method of producing an anti-CD38 antibody expressed from a polynucleotide encoding the HC of SEQ ID NO: 9 and the LC of SEQ ID NO: 10 having a G1F oligosaccharide content between about 15% and about 27%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and 74%.

The disclosure provides a method of producing an anti-CD38 antibody comprising the HC of SEQ ID NO: 9 and the LC of SEQ ID NO: 10 having a G1F oligosaccharide content between about 15% and about 27%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody comprising the HC of SEQ ID NO: 9 and the LC of SEQ ID NO: 10 having a G1F oligosaccharide content between about 15% and about 27%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
  culturing a host cell expressing the polynucleotide encoding the HC of SEQ ID NO: 9 and the LC of SEQ ID NO: 10 in conditions that the anti-CD38 antibody is produced; and
  controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, and a G0F oligosaccharide content between about 68% and about 74%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 68% and about 74%.

The disclosure also provides a method of producing an anti-CD38 antibody comprising the HC of SEQ ID NO: 9 and the LC of SEQ ID NO: 10 having a G1F oligosaccharide content between about 15% and about 25%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25%.

The disclosure also provides a method of producing an anti-CD38 antibody comprising the HC of SEQ ID NO: 9 and the LC of SEQ ID NO: 10 having a G1F oligosaccharide content between about 15% and about 25%, and a G0F oligosaccharide content between about 68% and about 74%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25% and the G0F oligosaccharide content between about 68% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, and a G0F oligosaccharide content between about 68% and about 74%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 68% and about 74%.

The disclosure also provides a method of producing an anti-CD38 antibody comprising the HC of SEQ ID NO: 9 and the LC of SEQ ID NO: 10 having a G1F oligosaccharide content between about 21% and about 25%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the HC of SEQ ID NO: 9 and the LC of SEQ ID NO: 10 having the G1F oligosaccharide content between about 21% and about 25%.

The disclosure also provides a method of producing an anti-CD38 antibody comprising the HC of SEQ ID NO: 9 and the LC of SEQ ID NO: 10 having a G1F oligosaccharide content between about 21% and about 25%, and a G0F oligosaccharide content between about 68% and about 74%, comprising:
culturing a host cell expressing the polynucleotide encoding the HC of SEQ ID NO: 9 and the LC of SEQ ID NO: 10 in conditions that the anti-CD38 antibody is produced; and
controlling the G1F oligosaccharide content of and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the HC of SEQ ID NO: 9 and the LC of SEQ ID NO: 10 having the G1F oligosaccharide content between about 21% and about 25% and the G0F oligosaccharide content between about 68% and about 74%.

The disclosure provides a method of producing an anti-CD38 antibody expressed from a polynucleotide encoding the VH of SEQ ID NO: 7 and the VL of SEQ ID NO: 8 having a G1F oligosaccharide content between about 15% and about 27%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the VH of SEQ ID NO: 7 and the VL of SEQ ID NO: 8 having the G1F oligosaccharide content between about 15% and about 27% and the G0F oligosaccharide content between about 65% and about 74%.

The disclosure provides a method of producing an anti-CD38 antibody comprising the VH of SEQ ID NO: 7 and the VL of SEQ ID NO: 8 having a G1F oligosaccharide content between about 15% and about 27%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%.

The disclosure also provides a method of producing an anti-CD38 antibody expressed from a polynucleotide encoding the VH of SEQ ID NO: 7 and the VL of SEQ ID NO: 8 having a G1F oligosaccharide content between about 15% and about 27%, and a G0F oligosaccharide content between about 65% and about 74%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody comprising the VH of SEQ ID NO: 7 and the VL of SEQ ID NO: 8 having a G1F oligosaccharide content between about 15% and about 27%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27%.

The disclosure also provides a method of producing an anti-CD38 antibody comprising the VH of SEQ ID NO: 7 and the VL of SEQ ID NO: 8 having a G1F oligosaccharide content between about 15% and about 27%, and a G0F oligosaccharide content between about 65% and about 74%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the VH of SEQ ID NO: 7 and the VL of SEQ ID NO: 8 having the G1F oligosaccharide content between about 15% and about 27% and the G0F oligosaccharide content between about 65% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:
culturing a CHO cell expressing the polynucleotide encoding the VH of SEQ ID NO: 7 and the VL of SEQ ID NO: 8 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 68% and about 74%.

The disclosure also provides a method of producing an anti-CD38 antibody comprising the VH of SEQ ID NO: 7 and the VL of SEQ ID NO: 8 having a G1F oligosaccharide content between about 15% and about 25%, comprising:
- culturing a CHO cell expressing the polynucleotide encoding the VH of SEQ ID NO: 7 and the VL of SEQ ID NO: 8 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25%.

The disclosure also provides a method of producing an anti-CD38 antibody comprising the VH of SEQ ID NO: 7 and the VL of SEQ ID NO: 8 having a G1F oligosaccharide content between about 15% and about 25%, and a G0F oligosaccharide content between about 68% and about 74%, comprising:
- culturing a CHO cell expressing the polynucleotide encoding the VH of SEQ ID NO: 7 and the VL of SEQ ID NO: 8 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the VH of SEQ ID NO: 7 and the VL of SEQ ID NO: 8 having the G1F oligosaccharide content between about 15% and about 25% and the G0F oligosaccharide content between about 68% and about 74%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, comprising:
- culturing a CHO cell expressing the polynucleotide encoding the VH of SEQ ID NO: 7 and the VL of SEQ ID NO: 8 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%.

The disclosure also provides a method of producing an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:
- culturing a CHO cell expressing the polynucleotide encoding the VH of SEQ ID NO: 7 and the VL of SEQ ID NO: 8 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 68% and about 74%.

The disclosure also provides a method of producing an anti-CD38 antibody comprising the VH of SEQ ID NO: 7 and the VL of SEQ ID NO: 8 having a G1F oligosaccharide content between about 21% and about 25%, comprising:
- culturing a CHO cell expressing the polynucleotide encoding the VH of SEQ ID NO: 7 and the VL of SEQ ID NO: 8 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25%.

The disclosure also provides a method of producing an anti-CD38 antibody comprising the VH of SEQ ID NO: 7 and the VL of SEQ ID NO: 8 having a G1F oligosaccharide content between about 21% and about 25%, and a G0F oligosaccharide content between about 68% and about 74%, comprising:
- culturing a CHO cell expressing the polynucleotide encoding the VH of SEQ ID NO: 7 and the VL of SEQ ID NO: 8 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the VH of SEQ ID NO: 7 and the VL of SEQ ID NO: 8 having the G1F oligosaccharide content between about 21% and about 25% and the G0F oligosaccharide content between about 68% and about 74%.

The disclosure provides a method of producing an anti-CD38 antibody expressed from a polynucleotide encoding the HC of SEQ ID NO: 9 and the LC of SEQ ID NO: 10 having a G1F oligosaccharide content between about 15% and about 27%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%.

The disclosure provides a method of producing an anti-CD38 antibody comprising the HC of SEQ ID NO: 9 and the LC of SEQ ID NO: 10 having a G1F oligosaccharide content between about 15% and about 27%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise about 8.5 ppb or less Mn, thereby producing the anti-CD38 antibody comprising the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody comprising the HC of SEQ ID NO: 9 and the LC of SEQ ID NO: 10 having a G1F oligosaccharide content between about 15% and about 27%, comprising:
- culturing a CHO cell expressing the polynucleotide encoding the HC of SEQ ID NO: 9 and the LC of SEQ ID NO: 10 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the HC of SEQ ID NO: 9 and the LC of SEQ ID NO: 10 having the G1F oligosaccharide content between about 15% and about 27%.

The disclosure also provides a method of producing an anti-CD38 antibody comprising the HC of SEQ ID NO: 9 and the LC of SEQ ID NO: 10 having a G1F oligosaccharide content between about 15% and about 27%, and a G0F oligosaccharide content between about 65% and about 74%, comprising:
- culturing a CHO cell expressing the polynucleotide encoding the HC of SEQ ID NO: 9 and the LC of SEQ ID NO: 10 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 8.5 ppb Mn, thereby producing the anti-CD38 antibody comprising the HC of SEQ ID NO: 9 and the LC of SEQ ID NO: 10 having the G1F oligosaccharide content between about 15% and about 27% and the G0F oligosaccharide content between about 65% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, comprising:
- culturing a CHO cell expressing the polynucleotide encoding the HC of SEQ ID NO: 9 and the LC of SEQ ID NO: 10 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 15% and about 25%, and a G0F oligosaccharide content between about 68% and about 74%, comprising:
- culturing a CHO cell expressing the polynucleotide encoding the HC of SEQ ID NO: 9 and the LC of SEQ ID NO: 10 in conditions that the anti-CD38 antibody is produced; and
- controlling the G1F oligosaccharide content and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 68% and about 74%.

The disclosure also provides a method of producing an anti-CD38 antibody comprising the HC of SEQ ID NO: 9 and the LC of SEQ ID NO: 10 having a G1F oligosaccharide content between about 15% and about 25%, comprising:
- culturing a CHO cell expressing the polynucleotide encoding the HC of SEQ ID NO: 9 and the LC of SEQ ID NO: 10 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25%.

The disclosure also provides a method of producing an anti-CD38 antibody comprising the HC of SEQ ID NO: 9 and the LC of SEQ ID NO: 10 having a G1F oligosaccharide content between about 15% and about 25%, and a G0F oligosaccharide content between about 68% and about 74%, comprising:
- culturing a CHO cell expressing the polynucleotide encoding the HC of SEQ ID NO: 9 and the LC of SEQ ID NO: 10 in conditions that the anti-CD38 antibody is produced; and
- controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 4.0 ppb and about 6.5 ppb Mn, thereby producing the anti-CD38 antibody comprising the HC of SEQ ID NO: 9 and the LC of SEQ ID NO: 10 having the G1F oligosaccharide content between about 15% and about 25% and the G0F oligosaccharide content between about 68% and about 74%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%.

The disclosure also provides a method of producing an anti-CD38 antibody expressed from a polynucleotide encoding the HC of SEQ ID NO: 9 and the LC of SEQ ID NO: 10 having a G1F oligosaccharide content between about 21% and about 25%, and a G0F oligosaccharide content between about 68% and about 74%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 68% and about 74%.

The disclosure also provides a method of producing an anti-CD38 antibody comprising the HC of SEQ ID NO: 9 and the LC of SEQ ID NO: 10 having a G1F oligosaccharide content between about 21% and about 25%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the HC of SEQ ID NO: 9 and the LC of SEQ ID NO: 10 having the G1F oligosaccharide content between about 21% and about 25%.

The disclosure also provides a method of producing an anti-CD38 antibody comprising the HC of SEQ ID NO: 9 and the LC of SEQ ID NO: 10 having a G1F oligosaccharide content between about 21% and about 25%, and a G0F oligosaccharide content between about 68% and about 74%, comprising:
culturing a CHO cell expressing the polynucleotide encoding the HC of SEQ ID NO: 9 and the LC of SEQ ID NO: 10 in conditions that the anti-CD38 antibody is produced; and
controlling the G1F oligosaccharide content of and the G0F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between about 5.0 ppb and about 6.5 ppb Mn, thereby producing the anti-CD38 antibody comprising the HC of SEQ ID NO: 9 and the LC of SEQ ID NO: 10 having the G1F oligosaccharide content between about 21% and about 25% and the G0F oligosaccharide content between about 68% and about 74%.

The disclosure also provides method of producing an anti-CD38 antibody having a G1F oligosaccharide content between about 15% and about 27%, comprising: culturing a host cell comprising a polynucleotide encoding the anti-CD38 antibody in a culture medium measured to comprise about 8.5 ppb or less Mn, thereby producing the anti-CD38 antibody having the G1F oligosaccharide content between about 15% and about 27%.

The disclosure also provides a method of producing an anti-CD38 antibody having a G1F oligosaccharide content between about 15% and about 27%, comprising: culturing a host cell comprising a polynucleotide encoding the anti-CD38 antibody in a culture medium controlled to comprise about 8.5 ppb or less Mn, thereby producing the anti-CD38 antibody having the G1F oligosaccharide content between about 15% and about 27%.

The disclosure also provides a method of producing an anti-CD38 antibody having a G1F oligosaccharide content between about 15% and about 27%, comprising: culturing a host cell comprising a polynucleotide encoding the anti-CD38 antibody in a culture medium comprising about 8.5 ppb or less Mn, and controlling the G1F oligosaccharide content by monitoring the concentration of Mn in the culture medium during biosynthesis of the antibody and regulating the concentration of Mn in the culture medium during biosynthesis of the antibody, thereby producing the antibody.

The disclosure also provides a method of producing an anti-CD38 antibody having a G1F oligosaccharide content between about 15% and 27%, comprising culturing a host cell transfected with a polynucleotide encoding the anti-CD38 antibody in a culture medium comprising about 8.0 ppb or less Mn, thereby producing the antibody.

The disclosure also provides a method of producing an anti-CD38 antibody having a G1F oligosaccharide content between about 15% and 27%, comprising: preparing a culture medium comprising about 8.5 ppb or less Mn; and culturing a host cell comprising a polynucleotide encoding the anti-CD38 antibody in the culture medium comprising about 8.5 ppb or less Mn, thereby producing the anti-CD38 antibody having the G1F oligosaccharide content between about 15% and 27%.

The disclosure also provides a method of producing an antibody having a G1F oligosaccharide content between about 15% and 27%, comprising: preparing a culture medium comprising about 8.0 ppb or less Mn; and culturing a host cell transfected with a polynucleotide encoding the antibody in the culture medium comprising about 8.0 ppb or less Mn, thereby producing the antibody.

The disclosure provides a method for controlling the G1F oligosaccharide content of an anti-CD38 antibody having a G1F oligosaccharide content between about 15% and 27% in a process for biosynthesizing the antibody in a culture medium, wherein the method comprises: monitoring a level of Mn in the culture medium during biosynthesis of the antibody; and regulating the level of Mn in the culture medium during biosynthesis of the antibody or antigen binding fragment thereof.

In some embodiments, the G1F oligosaccharide content of the anti-CD38 antibody is between about 15% and about 26%.

In some embodiments, the G1F oligosaccharide content of the anti-CD38 antibody is between about 15% and about 25%.

In some embodiments, the G1F oligosaccharide content of the anti-CD38 antibody is between about 16% and about 26%.

In some embodiments, the G1F oligosaccharide content of the anti-CD38 antibody is between about 17% and about 26%.

In some embodiments, the G1F oligosaccharide content of the anti-CD38 antibody is between about 18% and about 26%.

In some embodiments, the G1F oligosaccharide content of the anti-CD38 antibody is between about 19% and about 26%.

In some embodiments, the G1F oligosaccharide content of the anti-CD38 antibody is between about 20% and about 26%.

In some embodiments, the G1F oligosaccharide content of the anti-CD38 antibody is between about 21% and about 25%.

In some embodiments, the G0F content of the antibody is between about 68% and 74%.

In some embodiments, the G0F oligosaccharide content of the anti-CD38 antibody is between about 65% and 74%.

In some embodiments, the G0F oligosaccharide content of the anti-CD38 antibody is between about 66% and 74%.

In some embodiments, the G0F oligosaccharide content of the anti-CD38 antibody is between about 67% and 74%.

In some embodiments, the G0F oligosaccharide content of the anti-CD38 antibody is between about 68% and 74%.

In some embodiments, preparing the culture medium comprises measuring Mn concentration in one or more batches of raw material components used to prepare the culture medium and selecting those one or more batches of raw material components that in combination contain about 8.5 ppb or less Mn to prepare the culture medium.

In some embodiments, preparing the culture medium comprises measuring Mn concentration in one or more batches of raw material components used to prepare the culture medium and selecting those one or more batches of raw material components that in combination contain about 8.0 ppb or less Mn to prepare the culture medium.

In some embodiments, preparing the culture medium comprises measuring Mn concentration in one or more batches of raw material components used to prepare the culture medium and selecting those one or more batches of raw material components that in combination contain about 6.5 ppb or less Mn to prepare the culture medium.

In some embodiments, preparing the culture medium comprises measuring Mn concentration in one or more batches of raw material components used to prepare the culture medium and selecting those one or more batches of raw material components that in combination contain between about 4.0 ppb to about 8.5 ppb Mn to prepare the culture medium.

In some embodiments, preparing the culture medium comprises measuring Mn concentration in one or more batches of raw material components used to prepare the culture medium and selecting those one or more batches of raw material components that in combination contain between about 4.0 ppb to about 6.5 ppb Mn to prepare the culture medium.

In some embodiments, the culture medium is prepared to comprise about 8.0 ppb, about 7.5 ppb or less, about 7.0 ppb or less, about 6.5 ppb or less, about 6.0 ppb or less, about 5.5 ppb or less or about 5.5 ppb or less Mn.

In some embodiments, the culture medium is prepared to comprise about 8.5 ppb or less Mn.

In some embodiments, the culture medium is prepared to comprise about 8.0 ppb or less Mn.

In some embodiments, the culture medium is prepared to comprise about 7.5 ppb or less Mn.

In some embodiments, the culture medium is prepared to comprise about 7.0 ppb or less Mn.

In some embodiments, the culture medium is prepared to comprise about 6.5 ppb or less Mn.

In some embodiments, the culture medium is prepared to comprise about 6.0 ppb or less Mn.

In some embodiments, the culture medium is prepared to comprise about 5.5 ppb or less Mn.

In some embodiments, the culture medium is prepared to comprise about 5.0 ppb or less Mn.

In some embodiments, the culture medium is prepared to comprise between about 2 ppb and about 8.0 ppb Mn.

In some embodiments, the culture medium is prepared to comprise between about 2 ppb and about 8.5 ppb Mn.

In some embodiments, the culture medium is prepared to comprise between about 2 ppb and about 6.5 ppb Mn.

In some embodiments, the culture medium is prepared to comprise between about 5.0 ppb and about 8.0 ppb Mn.

In some embodiments, the culture medium is prepared to comprise between about 5.0 ppb and about 7.5 ppb Mn.

In some embodiments, the culture medium is prepared to comprise between about 5.0 ppb and about 7.0 ppb Mn.

In some embodiments, the culture medium is prepared to comprise between about 5.0 ppb and about 6.5 ppb Mn.

In some embodiments, the culture medium is prepared to comprise between about 4.0 ppb and about 6.5 ppb Mn.

In some embodiments, the culture medium is prepared to comprise between about 4.0 ppb and about 8.5 ppb Mn.

In some embodiments, the culture medium comprises about 8.5 ppb, 8.0 ppb, about 7.5 ppb or less, about 7.0 ppb or less, about 6.5 ppb or less, about 6.0 ppb or less, about 5.5 ppb or less or about 5.0 ppb or less Mn.

In some embodiments, the culture medium comprises about 8.5 ppb or less Mn.

In some embodiments, the culture medium comprises about 8.0 ppb or less Mn.

In some embodiments, the culture medium comprises about 7.5 ppb or less Mn.

In some embodiments, the culture medium comprises about 7.0 ppb or less Mn.

In some embodiments, the culture medium comprises about 6.5 ppb or less Mn.

In some embodiments, the culture medium comprises about 6.0 ppb or less Mn.

In some embodiments, the culture medium comprises about 5.5 ppb or less Mn.

In some embodiments, the culture medium comprises about 5.0 ppb or less Mn.

In some embodiments, the culture medium comprises between about 2 ppb and about 8.0 ppb Mn.

In some embodiments, the culture medium comprises between about 2 ppb and about 6.5 ppb Mn.

In some embodiments, the culture medium comprises between about 5.0 ppb and about 8.0 ppb Mn.

In some embodiments, the culture medium comprises between about 5.0 ppb and about 7.5 ppb Mn.

In some embodiments, the culture medium comprises between about 5.0 ppb and about 7.0 ppb Mn.

In some embodiments, the culture medium comprises between about 5.0 ppb and about 6.5 ppb Mn.

In some embodiments, the culture medium comprises between about 4.0 ppb and about 6.5 ppb Mn.

In some embodiments, the culture medium comprises between about 4.0 ppb and about 8.5 ppb Mn.

In some embodiments, the culture medium is controlled to comprise about 8.0 ppb, about 7.5 ppb or less, about 7.0 ppb or less, about 6.5 ppb or less, about 6.0 ppb or less, about 5.5 ppb or less or about 5.5 ppb or less Mn.

In some embodiments, the culture medium is controlled to comprise about 8.5 ppb or less Mn.

In some embodiments, the culture medium is controlled to comprise about 8.0 ppb or less Mn.

In some embodiments, the culture medium is controlled to comprise about 7.5 ppb or less Mn.

In some embodiments, the culture medium is controlled to comprise about 7.0 ppb or less Mn.

In some embodiments, the culture medium is controlled to comprise about 6.5 ppb or less Mn.

In some embodiments, the culture medium is controlled to comprise about 6.0 ppb or less Mn.

In some embodiments, the culture medium is controlled to comprise about 5.5 ppb or less Mn.

In some embodiments, the culture medium is controlled to comprise about 5.0 ppb or less Mn.

In some embodiments, the culture medium is controlled to comprise between about 2 ppb and about 8.0 ppb Mn.

In some embodiments, the culture medium is controlled to comprise between about 2 ppb and about 6.5 ppb Mn.

In some embodiments, the culture medium is controlled to comprise between about 5.0 ppb and about 8.0 ppb Mn.

In some embodiments, the culture medium is controlled to comprise between about 5.0 ppb and about 7.5 ppb Mn.

In some embodiments, the culture medium is controlled to comprise between about 5.0 ppb and about 7.0 ppb Mn.

In some embodiments, the culture medium is controlled to comprise between about 5.0 ppb and about 6.5 ppb Mn.

In some embodiments, the culture medium is controlled to comprise between about 4.0 ppb and about 6.5 ppb Mn.

In some embodiments, the culture medium is controlled to comprise between about 4.0 ppb and about 8.5 ppb Mn.

In some embodiments, the culture is a fed-batch culture. In some embodiments, the culture is a perfusion culture.

In some embodiments, the culture medium is a basal medium or a feed medium. In some embodiments, the culture medium is a basal medium. In some embodiments, the culture medium is a feed medium.

In some embodiments, the method is conducted under GMP-compliant conditions.

Any one or more culture media or combinations thereof may be used in the methods of the disclosure. Media are generally known and include Eagle's MEME (minimal essential media), Ham's F12, F-12 K medium, Dulbecco's medium, Dulbecco's Modified Eagle Medium, DMEM/Ham's F12 1:1, Trowell's T8, A2 media, Waymouth media, Williams E media, RPMI 1640, MCDB 104/110 media, Ventrex HL-1 media, albumin-globulin media, RPMI-1640 Medium, RPMI-1641 Medium, Iscove's Modified Dulbecco's Medium, McCoy's 5 A Medium, Leibovitz's L-15 Medium, and serum-free media such as EX-CELL™ 300 Series, protamine-zinc-insulin media (U.S. Pat. No. 4,072,565), biotin-folate media, transferrin-fatty acid media (U.S. Pat. No. 4,560,655), transferrin-EGF media (U.S. Pat. Nos. 4,615,977; 4,786,599), and other media permutations (U.S. Pat. Nos. 6,048,728; 7,294,484; 5,122,469; 5,976,833; 6,180,401; 5,856,179; 5,705,364; 7,666,416; 6,528,286; 6,924,124; 7,429,491) as well as other chemically defined medias. The media compositions are typically available through the vendor.

"Chemically defined media" refer to synthetic growth media in which the identity and concentration of all the components are known. Chemically defined media do not contain bacterial, yeast, animal, or plant extracts, animal serum or plasma although they may or may not include individual plant or animal-derived components (e.g., proteins, polypeptides, etc). Chemically defined media may contain inorganic salts such as phosphates, sulfates, and the like needed to support growth. The carbon source is defined, and is usually a sugar such as glucose, lactose, galactose, and the like, or other compounds such as glycerol, lactate, acetate, and the like. While certain chemically defined media also use phosphate salts as a buffer, other buffers may be employed such as citrate, triethanolamine, and the like. Examples of commercially available chemically defined media include ThermoFisher's CD Hybridoma Medium and CD Hybridoma AGT™ Medium, various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), combinations thereof, and the like. Methods of preparing chemically defined mediums are known in the art, for example in U.S. Pat. Nos. 6,171,825 and 6,936,441, Int. Pat. Publ. No. WO2007/077217, and U.S. Pat. Publ. No. US2008/0009040 and U.S. Pat. Publ. No. US2007/0212770. The exemplary culture media described herein may be used as a basal medium or a feed medium. Chemically-defined media feed designed to provide cell culture nutrients for fed-batch processes for culturing CHO cells include those available from IrivneScientific, such as BalanCD® CHO Feed powder or liquid media.

Exemplary components of a culture medium include essential and non-essential amino acids, vitamins, energy sources, lipids, and trace elements.

The methods of the disclosure may be used with any cell culture method that is amenable to the desired process (e.g., production of a recombinant antibody). Cells may be grown in batch or fed-batch cultures, where the culture is terminated after sufficient expression of the antibody, after which the expressed antibody is harvested. Alternatively, cells may be grown in batch-refeed, where the culture is not terminated, and new nutrients and other components are periodically or continuously added to the culture, during which the expressed antibody is harvested periodically or continuously. Other suitable methods (e.g., spin-tube cultures) are known in the art and may be used.

In some embodiments, the culture is a fed-batch culture. In some embodiments, the culture is a batch-refeed culture.

"Fed-batch culture" refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a base medium supplemented with feed media. Cells may be grown in any convenient volume. For example, cells may be grown in small scale reaction vessels ranging in volume from a few milliliters to several liters. Alternatively, cells may be grown in large scale commercial bioreactors ranging in volume from approximately at least 1 liter to 10, 50, 100, 250, 500, 1000, 2500, 5000, 8000, 10,000, 12,000, 15,000, 20000 or 25000 liters or more, or any volume in between.

Culture medium comprising about 8.5 ppb or less manganese may be prepared by analyzing manganese concentration in various batches of each raw material component of the culture media and selecting those batches of raw material components for making the culture media in which the manganese concentration is about 8.5 ppb or less or, when combined together, to total manganese concentration in the selected components is about 8.5 ppb or less. Culture medium comprising about 8.0 ppb or less manganese may be prepared by analyzing manganese concentration in various batches of each raw material component of the culture media and selecting those batches of raw material components for making the culture media in which the manganese concentration is about 8.0 ppb or less or, when combined together, to total manganese concentration in the selected components is about 8.0 ppb or less. Culture medium comprising about 6.5 ppb or less manganese may be prepared by analyzing manganese concentration in various batches of each raw material component of the culture media and selecting those batches of raw material components for making the culture media in which the manganese concentration is about 6.5 ppb or less or, when combined together, to total manganese concentration in the selected components is about 6.5 ppb or less. Manganese concentration may be measured in the raw materials components or media using methods described herein.

In some embodiments, the host cell is an eukaryotic cell. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as HD-BIOP3 GS Null CHO K1 (Horizon Discovery Limited, Cambridge, UK, CHO-K1SV (Lonza Biologics, Walkersville, Md.), CHO-K1 (ATCC CRL-61), DG44, CHO-S or CHO-DXB11.

In some embodiments, the host cell is a CHO cell, a PER.C6 cell, a NS0 cell, a Sp2/0 cell or a BHK cell.

In some embodiments, the CHO cell is a CHO-K1 cell, a CHO-DG44 cell, a CHO-S cell or a CHO-DXB11 cell.

In some embodiments, the CHO cell is deficient in glutamine synthetase (GS). Methods for use of GS as a selectable marker for mammalian cells are known.

In some embodiments, the method of the disclosure is conducted under GMP-compliant conditions.

In some embodiments, the anti-CD38 antibody comprises a heavy chain complementarity determining region 1 (HCDR1), a HCDR2, a HCDR3, a light chain complementarity determining region 1 (LCDR1), a LCDR2 and a LCDR3 of SEQ ID NOs: 1, 2, 3, 4, 5 and 6, respectively.

In some embodiments, the anti-CD38 antibody is expressed from a polynucleotide encoding the HCDR1, the HCDR2, the HCDR3, the LCDR1, the LCDR2 and the LCDR3 of SEQ ID NOs: 1, 2, 3, 4, 5 and 6, respectively.

In some embodiments, the anti-CD38 antibody comprises a heavy chain variable region (VH) of SEQ ID NO: 7 and a light chain variable region (VL) of SEQ ID NO: 8.

In some embodiments, the anti-CD38 antibody is expressed from a polynucleotide encoding the VH of SEQ ID NO: 7 and the VL of SEQ ID NO: 8.

In some embodiments, the anti-CD38 antibody is an IgG1 isotype. In some embodiments, the anti-CD38 antibody is an IgG2 isotype. In some embodiments, the anti-CD38 antibody is an IgG4 isotype.

In some embodiments, the anti-CD38 antibody comprises a heavy chain (HC) of SEQ ID NO: 9 and a light chain (LC) of SEQ ID NO: 10.

In some embodiments, the anti-CD38 antibody is expressed from a polynucleotide encoding the HC of SEQ ID NO: 9 and the LC of SEQ ID NO: 10.

In some embodiments, the anti-CD38 antibody is DARZALEX® (daratumumab).

In some embodiments, the anti-CD38 antibody is a biosimilar of DARZALEX® (daratumumab).

In some embodiments, the anti-CD38 antibody is MOR-202 (MOR-03087) comprising the VH and the VL of SEQ ID NOs: 11 and 12, respectively, as described in U.S. Pat. No. 8,088,896. The VH and the VL of MOR-202 may be expressed as IgG1/κ.

In some embodiments, the anti-CD38 antibody is isatuximab comprising the VH and the VL of SEQ ID NOs: 13 and 14, respectively, as described in U.S. Pat. No. 8,153,765. The VH and the VL of isatuximab may be expressed as IgG1/κ.

```
                                          SEQ ID NO: 1
SFAMS

SEQ ID NO: 2
AISGSGGGTYYADSVKG

SEQ ID NO: 3
DKILWFGEPVFDY

SEQ ID NO: 4
RASQSVSSYLA

SEQ ID NO: 5
DASNRAT

SEQ ID NO: 6
QQRSNWPPTF

SEQ ID NO: 7
EVQLLESGGGLVQPGGSLRLSCAVSGFTFNSFAMSWVRQAPGKGLEWV

SAISGSGGGTYYADSVKGRFTISRDNSKNTLYLQMNSLRAEDTAVYFC

AKDKILWFGEPVFDYWGQGTLVTVSS

SEQ ID NO: 8
EIVLTQSPATLSLSPGERATLSCRASQSVSSYLAWYQQKPGQAPRLLI

YDASNRATGIPARFSGSGSGTDFTLTISSLEPEDFAVYYCQQRSNWPP

TFGQGTKVEIK
```

SEQ ID NO: 9
EVQLLESGGGLVQPGGSLRLSCAVSGFTFNSFAMSWVRQAPGKGLEWV
SAISGSGGGTYYADSVKGRFTISRDNSKNTLYLQMNSLRAEDTAVYFC
AKDKILWFGEPVFDYWGQGTLVTVSSASTKGPSVFPLAPSSKSTSGGT
AALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPELL
GGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSV
MHEALHNHYTQKSLSLSPGK

SEQ ID NO: 10
EIVLTQSPATLSLSPGERATLSCRASQSVSSYLAWYQQKPGQAPRLLI
YDASNRATGIPARFSGSGSGTDFTLTISSLEPEDFAVYYCQQRSNWPP
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC

SEQ ID NO: 11
QVQLVESGGGLVQPGGSLRLSCAASGFTFSSYYMNWVRQAPGKGLEWV
SGISGDPSNTYYADSVKGRFTISRDNSKNTLYLQMNSLRAEDTAVYYC
ARDLPLVYTGFAYWGQGTLVTVSS

SEQ ID NO: 12
DIELTQPPSVSVAPGQTARISCSGDNLRHYYVYWYQQKPGQAPVLVIY
GDSKRPSGIPERFSGSNSGNTATLTISGTQAEDEADYYCQTYTGGASL
VFGGGTKLTVLGQ

SEQ ID NO: 13
QVQLVQSGAEVAKPGTSVKLSCKASGYTFTDYWMQWVKQRPGQGLEWI
GTIYPGDGDTGYAQKFQGKATLTADKSSKTVYMHLSSLASEDSAVYYC
ARGDYYGSNSLDYWGQGTSVTVSS

SEQ ID NO: 14
DIVMTQSHLSMSTSLGDPVSITCKASQDVSTVVAWYQQKPGQSPRRLI
YSASYRYIGVPDRFTGSGAGTDFTFTISSVQAEDLAVYYCQQHYSPPY
TFGGGTKLEIK

Methods of Measuring Oligosaccharide Composition of Antibodies

The oligosaccharide composition of antibodies may be determined with an HPLC method using an Agilent 1100/1200 Series HPLC System with Chemstation/Chemstore software. To quantitate the relative amounts of glycans, the N-linked oligosaccharides are first cleaved from the reduced and denatured test article with N-glycanase (PNGase F). The released glycans are labeled using anthranilic acid, purified by filtration using 0.45-μm nylon filters, and analyzed by HPLC with fluorescence detection. The HPLC chromatogram serves as a map that can be used to identify and quantitate the relative amounts of N-linked oligosaccharides present in the sample. Glycans are identified by co-elution with oligosaccharide standards and by retention time.

The amount of each glycan is quantitated by peak area integration and expressed as a percentage of total glycan peak area (peak area %). Results can be reported for G0F, G1F, G2F, total neutrals, and total charged glycans. Other neutral glycans may also be analyzed and are the sum of all integrated peaks eluting in the system between 17 and 35 minutes, excluding the peaks corresponding to G0F, G1F and G2F. Total neutral glycans are the sum of G0F, G1F, G2F and the other neutrals. Total charged glycans are the sum of all mono-sialylated glycan peaks eluting in the system between 42 and 55 minutes and all di-sialylated glycan peaks eluting between 78 and 90 minutes.

A mixture of oligosaccharide standards (G0F, G2F, G2F+ N-acetylneuraminic acid (NANA) and G2F+2NANA) are analyzed in parallel as a positive control for the labeling reaction, as standards for peak identification, and as a measure of system suitability. Reconstituted oligosaccharides from Prozyme, G0F (Cat. No. GKC-004301), G2F (Cat. No. GKC-024301), SA1F (Cat. No. GKC-124301), and SA2F (Cat. No. GKC-224301), or equivalent, are used as reference standards. A method blank negative control and pre-labeled G0F standard are also run for system suitability purposes.

Methods of Measuring Manganese Concentration in Media and Dry Powders

Manganese concentration in materials and solution may be measured using known methods and those described herein. Inductively coupled plasma mass spectrometry (ICP-MS) may be used to quantitate at parts per billion (ppb, μg/liter) trace metal concentrations in the test sample. An acid digestion procedure may be used to digest carbon rich sources to carbon dioxide and water before the sample is injected into an ICP-MS instrument such as the NexION® 350X ICP-MS (PerkinElmer). The wet chemical digestions may utilize different acids and oxidizing agents, such as nitric acid ($HNO_3$), hydrogen peroxide ($H_2O_2$), and hydrochloric acid (HCl).

Methods of Producing Antibodies

Methods of producing antibodies at large scales are known. Antibodies may be produced for example in CHO cells cultured using known methods. The antibody may be isolated and/or purified from culture medium by removing solids by centrifugation or filtering as a first step in the purification process. The antibody may be further purified by standard methods including chromatography (e.g., ion exchange, affinity, size exclusion, and hydroxyapatite chromatography), gel filtration, centrifugation, or differential solubility, ethanol precipitation or by any other available technique for the purification of antibodies. Protease inhibitors such as phenyl methyl sulfonyl fluoride (PMSF), leupeptin, pepstatin or aprotinin can be added at any or all stages in order to reduce or eliminate degradation of the antibody during the purification process. One of ordinary skill in the art will appreciate that the exact purification technique will vary depending on the character of the polypeptide or protein to be purified, the character of the cells from which the polypeptide or protein is expressed, and the composition of the medium in which the cells were grown.

Method of Producing a Drug Product

The methods disclosed herein also include methods of producing a drug product. For instance, the disclosure provides a method of producing a drug product comprising performing the steps of a method of producing an antibody as disclosed above herein.

The disclosure also provides a method of producing a drug product comprising an anti-CD38 antibody expressed from a polynucleotide encoding the VH of SEQ ID NO: 7 and the VL of SEQ ID NO: 8 and having a G1F oligosaccharide content between about 15% and about 27%, comprising:
  preparing a culture medium comprising about 8.5 ppb or less Mn;
  controlling the G1F oligosaccharide content of the anti-CD38 antibody by culturing a host cell comprising the polynucleotide encoding the VH of SEQ ID NO: 7 and the VL of SEQ ID NO: 8 in the culture medium prepared in step a), thereby producing the anti-CD38 antibody having the G1F oligosaccharide content between about 15% and about 27%; and
  formulating the anti-CD38 antibody as a drug product.

In some embodiments, the G1F oligosaccharide content of the anti-CD38 antibody is between about 15% and about 25%.

In some embodiments, the G1F oligosaccharide content of the anti-CD38 antibody is between about 21% and about 25%.

In some embodiments, a G0F oligosaccharide content of the anti-CD38 antibody is between about 65% and about 74%.

In some embodiments, the G0F oligosaccharide content of the anti-CD38 antibody is between about 68% and 74%.

In some embodiments, preparing the culture medium comprises measuring Mn concentration in one or more batches of raw material components used to prepare the culture medium and selecting those one or more batches of raw material components that in combination contain about 8.5 ppb or less Mn.

In some embodiments, the culture medium is prepared to comprise between about 4.0 ppb and about 8.5 ppb Mn.

In some embodiments, the culture medium is prepared to comprise between about 4.0 ppb and about 6.5 ppb Mn.

In some embodiments, the culture medium is prepared to comprise between about 5.0 ppb and about 6.5 ppb Mn.

In some embodiments, the G1F oligosaccharide content of the anti-CD38 antibody is between about 15% and about 27%, the G0F oligosaccharide content of the anti-CD38 antibody is between about 65% and about 74%, and the culture medium is prepared to comprise between about 4.0 ppb and about 8.5 ppb Mn.

In some embodiments, the G1F oligosaccharide content of the anti-CD38 antibody is between about 15% and about 25%, the G0F oligosaccharide content of the anti-CD38 antibody is between about 68% and about 74%, and the culture medium is prepared to comprise between about 4.0 ppb and about 6.5 ppb Mn.

In some embodiments, the G1F oligosaccharide content of the anti-CD38 antibody is between about 21% and about 25%, the G0F oligosaccharide content of the anti-CD38 antibody is between about 68% and about 74%, and the culture medium is prepared to comprise between about 5.0 ppb and about 6.5 ppb Mn.

In some embodiments, the culture medium is a basal medium or a feed medium.

In some embodiments, culturing comprises a fed-batch culture or a perfusion culture.

In some embodiments, the host cell is an eukaryotic cell.

In some embodiments, the eukaryotic cell is a CHO cell, a PER.C6 cell, a NS0 cell, a Sp2/0 cell or a BHK cell.

In some embodiments, the CHO cell is a CHO-K1 cell, a CHO-DG44 cell, a CHO-S cell or a CHO-DXB11 cell.

In some embodiments, the CHO cell is deficient in glutamine synthetase (GS).

In some embodiments, the method is conducted under GMP-compliant conditions.

In some embodiments, the anti-CD38 antibody comprises the VH of SEQ ID NO: 7 and the VL of SEQ ID NO: 9.

In some embodiments, the anti-CD38 antibody comprises an IgG1 isotype.

In some embodiments, the anti-CD38 antibody comprises the HC of SEQ ID NO: 9 and the LC of SEQ ID NO: 10.

In some embodiments, the anti-CD38 antibody is a biosimilar.

In some embodiments, formulating the drug product comprises formulating the anti-CD38 antibody at about 120 mg/mL in about 2,000 U/ml recombinant human hyaluronidase (rHuPH20), about 5 mM to about 15 mM histidine, about 100 mM to about 300 mM sorbitol, about 0.01% w/v to about 0.04% w/v PS-20 and about 1 mg/mL to about 2 mg/mL methionine, at a pH of about 5.6.

In some embodiments, formulating the drug product comprises formulating the anti-CD38 antibody at 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 27%, comprising:
  preparing a culture medium comprising about 8.5 ppb or less Mn;
  controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%; and
  formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:
  preparing a culture medium comprising about 8.5 ppb or less Mn;
  controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising about 8.5 ppb or less Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%; and
  formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 27%, comprising:
  preparing a culture medium comprising between about 4.0 ppb and about 8.5 ppb Mn;
  controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%; and formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:

preparing a culture medium comprising between about 4.0 ppb and about 8.5 ppb Mn; controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%; and formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 25%, comprising:

preparing a culture medium comprising between about 4.0 ppb and about 6.5 ppb Mn;

controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%; and formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:

preparing a culture medium comprising between about 4.0 ppb and about 6.5 ppb Mn;

controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 68% and about 74%; and formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 21% and about 25%, comprising:

preparing a culture medium comprising between about 5.0 ppb and about 6.5 ppb Mn;

controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%; and formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:

preparing a culture medium comprising between about 5.0 ppb and about 6.5 ppb Mn;

controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 68% and about 74%; and formulating the anti-CD38 antibody as a drug product.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 27%, comprising:

preparing a culture medium comprising between about 4.0 ppb and about 8.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%; and formulating the anti-CD38 antibody as a drug product.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:
preparing a culture medium comprising between about 4.0 ppb and about 8.5 ppb Mn;
controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%; and
formulating the anti-CD38 antibody as a drug product.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 25%, comprising:
preparing a culture medium comprising between about 4.0 ppb and about 6.5 ppb Mn;
controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%; and
formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:
preparing a culture medium comprising between about 4.0 ppb and about 6.5 ppb Mn;
controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 68% and about 74%; and
formulating the anti-CD38 antibody as a drug product.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 21% and about 25%, comprising:
preparing a culture medium comprising between about 5.0 ppb and about 6.5 ppb Mn;
controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%; and
formulating the anti-CD38 antibody as a drug product.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:
preparing a culture medium comprising between about 5.0 ppb and about 6.5 ppb Mn;
controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 68% and about 74%; and
formulating the anti-CD38 antibody as a drug product.

In some embodiments, the step of formulating the anti-CD38 antibody as a drug product comprises formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

In some embodiments, the step of formulating the anti-CD38 antibody as a drug product comprises formulating the anti-CD38 antibody at from about 20 mg/mL to about 180 mg/mL with recombinant human hyaluronidase (rHuPH20) in an amount of from about 30,000 U to about 45,000 U.

In some embodiments, the step of formulating the anti-CD38 antibody as a drug product comprises formulating the anti-CD38 antibody at about 120 mg/mL with about 30,000 U of rHuPH20.

In some embodiments, the step of formulating the anti-CD38 antibody as a drug product comprises formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6.

In some embodiments, the step of formulating the anti-CD38 antibody as a drug product comprises formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.5.

In some embodiments, the step of formulating the anti-CD38 antibody as a drug product comprises formulating the anti-CD38 antibody at from about 20 mg/mL to about 180 mg/mL with recombinant human hyaluronidase (rHuPH20) in an amount of from about 30,000 U to about 45,000 U, histidine at a concentration of from about 5 mM to about 15 mM, sorbitol at a concentration of from about 100 mM to about 300 mM, PS-20 at a concentration of from about 0.01% w/v to about 0.04% w/v; and methionine at a concentration of from about 1 mg/mL to about 2 mg/mL, at a pH of about 5.6.

In some embodiments, the step of formulating the anti-CD38 antibody as a drug product comprises formulating the anti-CD38 antibody at from about 20 mg/mL to about 180 mg/mL with recombinant human hyaluronidase (rHuPH20) in an amount of from about 30,000 U to about 45,000 U, histidine at a concentration of from about 5 mM to about 15 mM, sorbitol at a concentration of from about 100 mM to about 300 mM, PS-20 at a concentration of from about 0.01% w/v to about 0.04% w/v; and methionine at a concentration of from about 1 mg/mL to about 2 mg/mL, at a pH of about 5.5.

In some embodiments, the step of formulating the anti-CD38 antibody as a drug product comprises formulating the anti-CD38 antibody at about 120 mg/mL with about 2,000 U/ml of rHuPH20, 10 mM Histidine, about 300 mM Sorbitol, about 1 mg/mL methionine, about 0.04% Polysorbate 20, and about 2000 U/ml rHuPH20, at a pH of 5.6.

In some embodiments, the step of formulating the anti-CD38 antibody as a drug product comprises formulating the anti-CD38 antibody at about 120 mg/mL with about 2,000 U/ml of rHuPH20, 10 mM Histidine, about 300 mM Sorbitol, about 1 mg/mL methionine, about 0.04% Polysorbate 20, and about 2000 U/ml rHuPH20, at a pH of 5.5.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 27%, comprising:
  preparing a culture medium comprising between about 4.0 ppb and about 8.5 ppb Mn;
  controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%; and
  formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:
  preparing a culture medium comprising between about 4.0 ppb and about 8.5 ppb Mn;
  controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%; and
  formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 25%, comprising:
  preparing a culture medium comprising between about 4.0 ppb and about 6.5 ppb Mn;
  controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%; and
  formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:
  preparing a culture medium comprising between about 4.0 ppb and about 6.5 ppb Mn;
  controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 68% and about 74%; and
  formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 21% and about 25%, comprising:
  preparing a culture medium comprising between about 5.0 ppb and about 6.5 ppb Mn;
  controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:

preparing a culture medium comprising between about 5.0 ppb and about 6.5 ppb Mn;

controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 68% and about 74%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 27%, comprising:

preparing a culture medium comprising between about 4.0 ppb and about 8.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:

preparing a culture medium comprising between about 4.0 ppb and about 8.5 ppb Mn;

controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 25%, comprising:

preparing a culture medium comprising between about 4.0 ppb and about 6.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:

preparing a culture medium comprising between about 4.0 ppb and about 6.5 ppb Mn;

controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 68% and about 74%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 21% and about 25%, comprising:

preparing a culture medium comprising between about 5.0 ppb and about 6.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:

preparing a culture medium comprising between about 5.0 ppb and about 6.5 ppb Mn;

controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 68% and about 74%; and formulating the anti-CD38 antibody at about 20 mg/ml in about 25 mM acetic acid, about 60 mM sodium chloride, about 140 mM mannitol and about 0.04% w/v polysorbate-20 (PS-20); at pH about 5.5.

The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 27%, comprising:

preparing a culture medium comprising between about 4.0 ppb and about 8.5 ppb Mn;

controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6 The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 27%, and a G0F oligosaccharide content between about 65% and about 74%, comprising:

preparing a culture medium comprising between about 4.0 ppb and about 8.5 ppb Mn;

controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 8.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 27% and the G0F oligosaccharide content between about 65% and about 74%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6 The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 15% and about 25%, comprising:

preparing a culture medium comprising between about 4.0 ppb and about 6.5 ppb Mn;

controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6 The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:

preparing a culture medium comprising between about 4.0 ppb and about 6.5 ppb Mn;

controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 4.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 15% and about 25% and the G0F oligosaccharide content between about 68% and about 74%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6 The disclosure also provides a method of producing a drug product comprising an anti-CD38 antibody expressed from a polynucleotide encoding the VH of SEQ ID NO: 7 and the VL of SEQ ID NO: 8 having a G1F oligosaccharide content between about 21% and about 25%, comprising:

preparing a culture medium comprising between about 5.0 ppb and about 6.5 ppb Mn;

controlling the G1F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6 The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:

preparing a culture medium comprising between about 5.0 ppb and about 6.5 ppb Mn;

controlling the G1F oligosaccharide content and the G0F oligosaccharide content of the anti-CD38 antibody by culturing a CHO cell comprising the polynucleotide encoding the VH of SEQ ID NO: 7 and the VL of SEQ ID NO: 8 in the culture medium comprising between about 5.0 ppb and about 6.5 ppb Mn, thereby producing the anti-CD38 antibody expressed from the polynucleotide encoding the VH of SEQ ID NO: 7 and the VL of SEQ ID NO: 8 having the G1F oligosaccharide content between about 21% and about 25% and the G0F oligosaccharide content between about 68% and about 74%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 27%, comprising:

preparing a culture medium comprising between about 4.0 ppb and about 8.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 27%, and a G0F oligosaccharide content between about 65% and about 74%, comprising:

preparing a culture medium comprising between about 4.0 ppb and about 8.5 ppb Mn;

controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 8.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 27% and the G0F oligosaccharide content between about 65% and about 74%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 15% and about 25%, comprising:

preparing a culture medium comprising between about 4.0 ppb and about 6.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 15% and about 25%, and a G0F oligosaccharide content between about 68% and about 74%, comprising:

preparing a culture medium comprising between about 4.0 ppb and about 6.5 ppb Mn;

controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 4.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 15% and about 25% and the G0F oligosaccharide content between about 68% and about 74%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6

The disclosure also provides a method of producing a drug product comprising an anti-CD38 antibody expressed from a polynucleotide encoding the HC of SEQ ID NO: 9 and the LC of SEQ ID NO: 10 having a G1F oligosaccharide content between about 21% and about 25%, comprising:

preparing a culture medium comprising between about 5.0 ppb and about 6.5 ppb Mn;

controlling the G1F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6.

The disclosure also provides a method of producing a drug product comprising an anti-CD38 antibody expressed from a polynucleotide encoding the VH of SEQ ID NO: 7 and the VL of SEQ ID NO 8 having a G1F oligosaccharide content between about 21% and about 25%, and a G0F oligosaccharide content between about 68% and about 74%, comprising:

preparing a culture medium comprising between about 5.0 ppb and about 6.5 ppb Mn;

controlling the G1F oligosaccharide content and the G0F oligosaccharide content of the anti-CD38 antibody by culturing a CHO cell comprising the polynucleotide encoding the HC of SEQ ID NO: 9 and the LC of SEQ ID NO: 10 in the culture medium comprising between about 5.0 ppb and about 6.5 ppb Mn, thereby producing the anti-CD38 antibody expressed from the polynucleotide encoding the HC of SEQ ID NO: 9 and the LC of SEQ ID NO: 10 having the G1F oligosaccharide content between about 21% and about 25% and the G0F oligosaccharide content between about 68% and about 74%; and formulating the anti-CD38 antibody at about 120 mg/mL with about 2,000 U/ml of rHuPH20, histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.6

Compositions of Matter

The disclosure also provides a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and about 27%, wherein the drug substance is manufactured using the process comprising: culturing a host cell comprising a polynucleotide encoding the HCDR1, the HCDR2, the HCDR3, the LCDR1, the LCDR2 and the LCDR3 of SEQ ID NOs: 1, 2, 3, 4, 5, and 6, respectively, in a culture medium measured to comprise about 8.5 ppb or less Mn, thereby producing the drug substance comprising the anti-CD38 antibody having the G1F oligosaccharide content between about 15% and about 27%.

The disclosure also provides a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising: culturing a CHO cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in a culture medium comprising about 8.0 ppb or less Mn, thereby producing the drug substance.

The disclosure also provides drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and about 27%, wherein the drug substance is manufactured using the process comprising: preparing a culture medium comprising about 8.5 ppb or less Mn; and culturing a host cell comprising a polynucleotide encoding the HCDR1, the HCDR2, the HCDR3, the LCDR1, the LCDR2 and the LCDR3 of SEQ ID NOs: 1, 2, 3, 4, 5, and 6, respectively, in culture medium comprising about 8.5 ppb or less Mn, thereby producing the drug substance comprising the anti-CD38 antibody having the G1F oligosaccharide content between about 15% and about 27%.

The disclosure also provides a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising preparing a culture medium comprising about 8.0 ppb or less Mn; and culturing a host cell comprising a polynucleotide encoding the HCDR1, the HCDR2, the HCDR3, the LCDR1, the LCDR2 and the LCDR3 of SEQ ID NOs: 1, 2, 3, 4, 5, and 6, respectively, in culture medium comprising about 8.0 ppb or less Mn, thereby producing the drug substance.

In some embodiments, the anti-CD38 antibody comprises a VH of SEQ ID NO: 7 and a VL of SEQ ID NO: 8 and the host cell comprises a polynucleotide encoding the VH of SEQ ID NO: 7 and the VL of SEQ ID NO: 8.

In some embodiments, the anti-CD38 antibody comprises a HC of SEQ ID NO: 9 and a LC of SEQ ID NO: 10 and the host cell comprises a polynucleotide encoding the HC of SEQ ID NO: 9 and the LC of SEQ ID NO: 10.

In some embodiments, the G1F oligosaccharide content of the anti-CD38 antibody is between about 16% and about 26%. In some embodiments, the G1F oligosaccharide content of the anti-CD38 antibody is between about 17% and about 26%. In some embodiments, the G1F oligosaccharide content of the anti-CD38 antibody is between about 18% and about 26%. In some embodiments, the G1F oligosaccharide content of the anti-CD38 antibody is between about 19% and about 26%. In some embodiments, the G1F oligosaccharide content of the anti-CD38 antibody is between about 20% and about 26%. In some embodiments, the G1F oligosaccharide content of the anti-CD38 antibody is between about 21% and about 25%.

In some embodiments, the G0F content of the anti-CD38 antibody is between about 65% and about 74%.

In some embodiments, the G0F oligosaccharide content of the anti-CD38 antibody is between about 66% and 74%. In some embodiments, the G0F oligosaccharide content of the anti-CD38 antibody is between about 67% and about 74%. In some embodiments, the G0F oligosaccharide content of the anti-CD38 antibody is between about 68% and about 74%.

The disclosure also provides a drug substance comprising an anti-CD38 antibody comprising a VH of SEQ ID NO: 7 and a VL of SEQ ID NO: 8, and having a G1F oligosaccharide content between about 15% and 27%, wherein the drug substance is manufactured using the process comprising: culturing a host cell transfected with a polynucleotide encoding the VH of SEQ ID NO: 7 and the VL of SEQ ID NO: 8 in a culture medium measured to comprise about 8.5 ppb or less Mn, thereby producing the drug substance comprising the anti-CD38 antibody having the G1F oligosaccharide content between about 15% and about 27%.

The disclosure also provides a drug substance comprising an anti-CD38 antibody comprising a VH of SEQ ID NO: 7 and a VL of SEQ ID NO: 8, and having a G1F oligosaccharide content between about 15% and 27%, wherein the drug substance is manufactured using the process comprising: preparing a culture medium comprising about 8.0 ppb or less Mn; and culturing a host cell comprising a polynucleotide encoding the VH of SEQ ID NO: 7 and the VL of SEQ ID NO: 8 in culture medium comprising about 8.5 ppb or less Mn, thereby producing the drug substance The disclosure also provides a drug substance comprising an anti-CD38 antibody comprising a VH of SEQ ID NO: 7 and a VL of SEQ ID NO: 8 and having a G1F oligosaccharide content between about 15% and about 27%, wherein the drug substance is manufactured using the process comprising: preparing a culture medium comprising about 8.5 ppb or less Mn; and culturing a host cell transfected with a polynucleotide encoding the VH of SEQ ID NO 7 and the VL of SEQ ID NO: 8 in culture medium comprising about 8.5 ppb or less Mn, thereby producing the drug substance comprising the anti-CD38 antibody having the G1F oligosaccharide content between about 15% and about 27%.

The disclosure also provides a drug substance comprising an anti-CD38 antibody comprising a VH of SEQ ID NO: 7 and a VL of SEQ ID NO: 8, respectively, and having a G1F oligosaccharide content between about 15% and 27%, wherein the drug substance is manufactured using the process comprising: preparing a culture medium comprising about 8.0 ppb or less Mn; and culturing a host cell comprising a polynucleotide encoding the VH of SEQ ID NO: 7 and the VL of SEQ ID NO: 8 in culture medium comprising about 8.0 ppb or less Mn, thereby producing the drug substance.

The disclosure also provides a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising: culturing a host cell transfected with a polynucleotide encoding the HC of SEQ ID NO: 9 and a LC of SEQ ID NO: 10 a culture medium measured to comprise about 8.5 ppb or less Mn, thereby producing the drug substance comprising the anti-CD38 antibody having the G1F oligosaccharide content between about 15% and about 27%.

The disclosure also provides a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising culturing a CHO cell transfected with a polynucleotide encoding the HC of SEQ ID NO: 9 and the LC of SEQ ID NO: 10 in a culture medium comprising about 8.0 ppb or less Mn, thereby producing the drug substance.

The disclosure also provides a drug substance comprising an anti-CD38 antibody comprising a HC of SEQ ID NO: 9 and a LC of SEQ ID NO: 10, and having a G1F oligosaccharide content between about 15% and 27%, wherein the drug substance is manufactured using the process comprising: preparing a culture medium comprising about 8.5 ppb or less Mn; and culturing a host cell transfected with a polynucleotide encoding the HC of SEQ ID NO: 9 and a LC of SEQ ID NO: 10 in culture medium comprising about 8.5 ppb or less Mn, thereby producing the drug substance comprising the anti-CD38 antibody having the G1F oligosaccharide content between about 15% and about 27%.

The disclosure also provides a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising: preparing a culture medium comprising about 8.0 ppb or less Mn; and culturing a host cell comprising a polynucleotide encoding the HC of SEQ ID NO: 9 and the LC of SEQ ID NO: 10, in culture medium comprising about 6.5 ppb or less Mn, thereby producing the drug substance.

The disclosure also provides a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising: culturing a CHO cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in a culture medium comprising about 6.5 ppb or less Mn, thereby producing the drug substance.

The disclosure also provides a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising: preparing a culture medium comprising about 6.5 ppb or less Mn; and culturing a host cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in culture medium comprising about 6.5 ppb or less Mn, thereby producing the drug substance.

The disclosure also provides a drug substance comprising an anti-CD38 antibody comprising a VH of SEQ ID NO: 7 and a VL of SEQ ID NO: 8, respectively, and having a G1F oligosaccharide content between about 15% and 27%, wherein the drug substance is manufactured using the process comprising: culturing a CHO cell transfected with a polynucleotide encoding the VH of SEQ ID NO: 7 and the VL of SEQ ID NO: 8 in a culture medium comprising about 6.5 ppb or less Mn, thereby producing the drug substance.

The disclosure also provides a drug substance comprising an anti-CD38 antibody comprising a VH of SEQ ID NO: 7 and a VL of SEQ ID NO: 8, respectively, and having a G1F oligosaccharide content between about 15% and 27%, wherein the drug substance is manufactured using the process comprising: preparing a culture medium comprising about 6.5 ppb or less Mn; and culturing a host cell transfected with a polynucleotide encoding the VH of SEQ ID NO: 7 and the VL of SEQ ID NO: 8 in culture medium comprising about 6.5 ppb or less Mn, thereby producing the drug substance.

The disclosure also provides a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising: culturing a CHO cell transfected with a polynucleotide encoding the HC of SEQ ID NO: 9 and the LC of SEQ ID NO: 10 in a culture medium comprising about 6.5 ppb or less Mn, thereby producing the drug substance.

The disclosure also provides a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising: preparing a culture medium comprising about 6.5 ppb or less Mn; and culturing a host cell transfected with a polynucleotide encoding the HC of SEQ ID NO: 9 and the LC of SEQ ID NO: 10, in culture medium comprising about 6.5 ppb or less Mn, thereby producing the drug substance.

In some embodiments, the culture medium is prepared by measuring Mn concentration in one or more batches of raw material components used to prepare the culture medium and selecting those one or more batches of raw material components that in combination contain about 8.5 ppb or less Mn to prepare the culture medium.

In some embodiments, the culture medium is prepared by measuring Mn concentration in one or more batches of raw material components used to prepare the culture medium and selecting those one or more batches of raw material components that in combination contain about 8.0 ppb or less Mn to prepare the culture medium.

In some embodiments, the culture medium comprises about 8.0 ppb, about 7.5 ppb or less, about 7.0 ppb or less, about 6.5 ppb or less, about 6.0 ppb or less, about 5.5 ppb or less or about 5.0 ppb or less Mn.

In some embodiments, the culture medium comprises about 8.0 ppb or less Mn.

In some embodiments, the culture medium comprises about 7.5 ppb or less Mn.

In some embodiments, the culture medium comprises about 7.0 ppb or less Mn.

In some embodiments, the culture medium comprises about 6.5 ppb or less Mn.

In some embodiments, the culture medium comprises about 6.0 ppb or less Mn.

In some embodiments, the culture medium comprises about 5.5 ppb or less Mn.

In some embodiments, the culture medium comprises about 5.0 ppb or less Mn.

In some embodiments, the culture medium comprises between about 2 ppb and about 8.0 ppb Mn.

In some embodiments, the culture medium comprises between about 2 ppb and about 6.5 ppb Mn.

In some embodiments, the culture medium comprises between about 5.0 ppb and about 8.0 ppb Mn.

In some embodiments, the culture medium comprises between about 5.0 ppb and about 7.5 ppb Mn.

In some embodiments, the culture medium comprises between about 5.0 ppb and about 7.0 ppb Mn.

In some embodiments, the culture medium comprises between about 5.0 ppb and about 6.5 ppb Mn.

In some embodiments, the culture medium is a basal medium or a feed medium. In some embodiments, the culture medium is a basal medium. In some embodiments, the culture medium is a feed medium.

In some embodiments, the culture is a fed-batch culture. In some embodiments, the culture is a perfusion culture.

In some embodiments, the host cell is an eukaryotic cell.

In some embodiments, the eukaryotic cell is a CHO cell, a PER.C6 cell, a NS0 cell, a Sp2/0 cell or a BHK cell.

In some embodiments, the CHO cell is deficient in glutamine synthetase (GS).

In some embodiments, the CHO cell is a CHO-K1 cell, a CHO-DG44 cell, a CHO-S cell or a CHO-DXB11 cell.

In some embodiments, the drug substance is manufactured under GMP-compliant conditions.

The disclosure also provides a drug product produced by the methods of the disclosure.

The disclosure also provides a drug product comprising the drug substance of the disclosure.

The disclosure also provides a drug product comprising an anti-CD38 antibody having a GU' oligosaccharide content between about 15% and 27%, wherein the anti-CD38 antibody is produced by a process comprising: culturing a host cell comprising a polynucleotide encoding the anti-CD38 antibody in a culture medium measured to comprise about 8.5 ppb or less Mn, thereby producing the anti-CD38 antibody having the GU' oligosaccharide content between about 15% and about 27%.

In some embodiments, the GU' oligosaccharide content of the anti-CD38 antibody is between about 16% and about 26%. In some embodiments, the GU' oligosaccharide content of the anti-CD38 antibody is between about 17% and about 26%. In some embodiments, the GU' oligosaccharide content of the anti-CD38 antibody is between about 18% and about 26%. In some embodiments, the GU' oligosaccharide content of the anti-CD38 antibody is between about 19% and about 26%. In some embodiments, the GU' oligosaccharide content of the anti-CD38 antibody is between about 20% and about 26%. In some embodiments, the GU' oligosaccharide content of the anti-CD38 antibody is between about 21% and about 25%.

In some embodiments, a G0F oligosaccharide content of the anti-CD38 antibody is between about 65% and about 74%. In some embodiments, the G0F oligosaccharide content of the anti-CD38 antibody is between about 66% and 74%. In some embodiments, the G0F oligosaccharide content of the anti-CD38 antibody is between about 67% and about 74%. In some embodiments, the G0F oligosaccharide content of the anti-CD38 antibody is between about 68% and about 74%.

In some embodiments, the culture medium is prepared by measuring Mn concentration in one or more batches of raw material components used to prepare the culture medium and selecting those one or more batches of raw material components that in combination contain about 8.5 ppb or less Mn to prepare the culture medium.

In some embodiments, the culture medium comprises about 8.0 ppb, about 7.5 ppb or less, about 7.0 ppb or less, about 6.5 ppb or less, about 6.0 ppb or less, about 5.5 ppb or less or about 5.0 ppb or less Mn.

In some embodiments, the culture medium comprises about 8.0 ppb or less Mn.

In some embodiments, the culture medium comprises about 7.5 ppb or less Mn.

In some embodiments, the culture medium comprises about 7.0 ppb or less Mn.

In some embodiments, the culture medium comprises about 6.5 ppb or less Mn.

In some embodiments, the culture medium comprises about 6.0 ppb or less Mn.

In some embodiments, the culture medium comprises about 5.5 ppb or less Mn.

In some embodiments, the culture medium comprises about 5.0 ppb or less Mn.

In some embodiments, the culture medium comprises between about 2 ppb and about 8.0 ppb Mn.

In some embodiments, the culture medium comprises between about 2 ppb and about 6.5 ppb Mn.

In some embodiments, the culture medium comprises between about 5.0 ppb and about 8.0 ppb manganese.

In some embodiments, the culture medium comprises between about 5.0 ppb and about 7.5 ppb manganese.

In some embodiments, the culture medium comprises between about 5.0 ppb and about 7.0 ppb manganese.

In some embodiments, the culture medium comprises between about 5.0 ppb and about 6.5 ppb manganese.

In some embodiments, the culture medium is a basal medium or a feed medium. In some embodiments, the culture medium is a basal medium. In some embodiments, the culture medium is a feed medium.

In some embodiments, the culture is a fed-batch culture. In some embodiments, the culture is a perfusion culture.

In some embodiments, the host cell is an eukaryotic cell.

In some embodiments, the eukaryotic cell is a CHO cell, a PER.C6 cell, a NS0 cell, a Sp2/0 cell or a BHK cell.

In some embodiments, the CHO cell is deficient in glutamine synthetase (GS).

In some embodiments, the CHO cell is a CHO-K1 cell, a CHO-DG44 cell, a CHO-S cell or a CHO-DXB11 cell.

In some embodiments, the drug product is manufactured under GMP-compliant conditions.

In some embodiments, the drug product comprises the anti-CD38 antibody comprising the HCDR1, the HCDR2, the HCDR3, the LCDR1, the LCDR2 and the LCDR3 of SEQ ID NOs: 1, 2, 3, 4, 5 and 6, respectively.

In some embodiments, the drug product comprises the anti-CD38 antibody comprising the VH of SEQ ID NO: 7 and the VL of SEQ ID NO: 8.

In some embodiments, the drug product comprises the anti-CD38 antibody comprising the HC of SEQ ID NO: 9 and LC of SEQ ID NO: 10.

In some embodiments, the drug product is a reference product.

In some embodiments, the drug product is a biosimilar.

In some embodiments, the drug product is a biosimilar of DARZALEX® (daratumumab).

In some embodiments, the drug product comprises about 20 mg/ml of the anti-CD38 antibody formulated in about 25 mM acetic acid, about 60 mM sodium chloride, about 140 mM mannitol and about 0.04% w/v polysorbate-20 (PS-20); at pH about 5.5.

In some embodiments, the drug product comprises from about 20 mg/mL to about 180 mg/mL of the anti-CD38 antibody and recombinant human hyaluronidase (rHuPH20) in an amount of from about 30,000 U to about 45,000 U.

In some embodiments, the drug product comprises from about 1 mg/mL to about 180 mg/mL of the anti-CD38 antibody.

In some embodiments, the drug product comprises from about 10 mg/mL to about 180 mg/mL of the anti-CD38 antibody.

In some embodiments, the drug product comprises from about 20 mg/mL to about 160 mg/mL of the anti-CD38 antibody.

In some embodiments, the drug product comprises from about 20 mg/mL to about 140 mg/mL of the anti-CD38 antibody.

In some embodiments, the drug product comprises from about 20 mg/mL to about 120 mg/mL of the anti-CD38 antibody.

In some embodiments, the drug product comprises from about 40 mg/mL to about 120 mg/mL of the anti-CD38 antibody.

In some embodiments, the drug product comprises from about 60 mg/mL to about 120 mg/mL of the anti-CD38 antibody.

In some embodiments, the drug product comprises from about 80 mg/mL to about 120 mg/mL of the anti-CD38 antibody.

In some embodiments, the drug product comprises from about 100 mg/mL to about 120 mg/mL of the anti-CD38 antibody.

In some embodiments, the drug product comprises about 1 mg/mL, about 5 mg/mL, about 10 mg/mL, about 15 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL or about 180 mg/mL of the anti-CD38 antibody.

In some embodiments, the drug product comprises about 20 mg/mL of the anti-CD38 antibody.

In some embodiments, the drug product comprises about 100 mg/mL of the anti-CD38 antibody.

In some embodiments, the drug product comprises about 120 mg/mL of the anti-CD38 antibody.

In some embodiments, the drug product comprises from about 50 U/mL to about 5,000 U/mL of the rHuPH20.

In some embodiments, the drug product comprises from about 500 U/mL to about 5,000 U/mL of the rHuPH20.

In some embodiments, the drug product comprises from about 1,000 U/mL to about 5,000 U/mL of the rHuPH20.

In some embodiments, the drug product comprises from about 2,000 U/mL to about 5,000 U/mL of the rHuPH20.

In some embodiments, the drug product comprises from about 50 U/mL to about 2,000 U/mL of the rHuPH20.

In some embodiments, the drug product comprises from about 500 U/mL to about 2,000 U/mL of the rHuPH20.

In some embodiments, the drug product comprises from about 1,000 U/mL to about 2,000 U/mL of the rHuPH20.

In some embodiments, the drug product comprises about 500 U/mL, about 600 U/mL, about 700 U/mL, about 800 U/mL, about 900 U/mL, about 1,000 U/mL, about 1,100 U/mL, about 1,200 U/mL, about 1,300 U/mL, about 1,400 U/mL, about 1,500 U/mL, about 1,600 U/mL, about 1,700 U/mL, about 1,800 U/mL, about 1,900 U/mL, about 2,000 U/mL, about 2,100 U/mL, about 2,200 U/mL, about 2,300 U/mL, about 2,400 U/mL, about 2,500 U/mL, about 2,600 U/mL, about 2,700 U/mL, about 2,800 U/mL, about 2,900 U/mL, about 3,000 U/mL, about 3,100 U/mL, about 3,200 U/mL, about 3,300 U/mL, about 3,400 U/mL, about 3,500 U/mL, about 3,600 U/mL, about 3,700 U/mL, about 3,800 U/mL, about 3,900 U/mL, about 4,000 U/mL, about 4,100 U/mL, about 4,200 U/mL, about 4,300 U/mL, about 4,400 U/mL, about 4,500 U/mL, about 4,600 U/mL, about 4,700 U/mL, about 4,800 U/mL, about 4,900 U/mL or about 5,000 U/mL of the rHuPH20.

In some embodiments, the drug product comprises about 500 U/mL of the rHuPH20.

In some embodiments, the drug product comprises about 2,000 U/mL of the rHuPH20.

In some embodiments, the drug product comprises about 5,000 U/mL of the rHuPH20.

In some embodiments, the drug product comprises from about 1,200 mg to about 5,000 mg of the anti-CD38 antibody.

In some embodiments, the drug product comprises from about 1,200 mg to about 2,400 mg of the anti-CD38 antibody.

In some embodiments, the drug product comprises from about 1,200 mg to about 1,800 mg of the anti-CD38 antibody.

In some embodiments, the drug product comprises about 1,200 mg of the anti-CD38 antibody.

In some embodiments, the drug product comprises about 1,400 mg of the anti-CD38 antibody.

In some embodiments, the drug product comprises about 1,600 mg of the anti-CD38 antibody.

In some embodiments, the drug product comprises about 1,800 mg of the anti-CD38 antibody.

In some embodiments, the drug product comprises about 2,000 mg of the anti-CD38 antibody.

In some embodiments, the drug product comprises about 2,200 mg of the anti-CD38 antibody.

In some embodiments, the drug product comprises about 2,400 mg of the anti-CD38 antibody.

In some embodiments, the drug product comprises about 2,600 mg of the anti-CD38 antibody.

In some embodiments, the drug product comprises about 2,800 mg of the anti-CD38 antibody.

In some embodiments, the drug product comprises about 3,000 mg of the anti-CD38 antibody.

In some embodiments, the drug product comprises about 3,500 mg of the anti-CD38 antibody.

In some embodiments, the drug product comprises about 4,000 mg of the anti-CD38 antibody.

In some embodiments, the drug product comprises about 4,500 mg of the anti-CD38 antibody.

In some embodiments, the drug product comprises about 5,000 mg of the anti-CD38 antibody.

In some embodiments, the drug product comprises from about 750 U to about 75,000 U of the rHuPH20.

In some embodiments, the drug product comprises from about 7,500 U to about 45,000 U of the rHuPH20.

In some embodiments, the drug product comprises from about 30,000 U to about 45,000 U of the rHuPH20.

In some embodiments, the drug product comprises about 7,500 U, about 8,000 U, about 8,500 U, about 9,000 U, about 10,000 U, about 15,000 U, about 20,000 U, about 21,000 U, about 22,000 U, about 23,000 U, about 24,000 U, about 25,000 U, about 26,000 U, about 27,000 U, about 28,000 U, about 29,000 U, about 30,000 U, about 31,000 U, about 32,000 U, about 33,000 U, about 34,000 U, about 35,000 U, about 36,000 U, about 37,000 U, about 38,000 U, about 39,000 U, about 40,000 U, about 41,000 U, about 42,000 U, about 43,000 U, about 44,000 U, about 45,000 U, about 46,000 U, about 47,000 U, about 48,000 U, about 49,000 U, about 50,000 U, about 55,000 U, about 60,000 U, about 65,000 U, about 70,000 U or about 75,000 U of the rHuPH20.

In some embodiments, the drug product comprises about 5,000 mg of the anti-CD38 antibody and about 30,000 U of the rHuPH20.

In some embodiments, the drug product comprises about 5,000 mg of the anti-CD38 antibody and about 45,000 U of the rHuPH20.

In some embodiments, the drug product comprises about 3,000 mg of the anti-CD38 antibody and about 30,000 U of the rHuPH20.

In some embodiments, the drug product comprises about 3,000 mg of the anti-CD38 antibody and about 45,000 U of the rHuPH20.

In some embodiments, the drug product comprises about 2,800 mg of the anti-CD38 antibody and about 30,000 U of the rHuPH20.

In some embodiments, the drug product comprises about 2,800 mg of the anti-CD38 antibody and about 45,000 U of the rHuPH20.

In some embodiments, the drug product comprises about 2,600 mg of the anti-CD38 antibody and about 30,000 U of the rHuPH20.

In some embodiments, the drug product comprises about 2,600 mg of the anti-CD38 antibody and about 45,000 U of the rHuPH20.

In some embodiments, the drug product comprises about 2,400 mg of the anti-CD38 antibody and about 30,000 U of the rHuPH20.

In some embodiments, the drug product comprises about 2,400 mg of the anti-CD38 antibody and about 45,000 U of the rHuPH20.

In some embodiments, the drug product comprises about 2,200 mg of the anti-CD38 antibody and about 30,000 U of the rHuPH20.

In some embodiments, the drug product comprises about 2,200 mg of the anti-CD38 antibody and about 45,000 U of the rHuPH20.

In some embodiments, the drug product comprises about 2,000 mg of the anti-CD38 antibody and about 30,000 U of the rHuPH20.

In some embodiments, the drug product comprises about 2,000 mg of the anti-CD38 antibody and about 45,000 U of the rHuPH20.

In some embodiments, the drug product comprises about 1,800 mg of the anti-CD38 antibody and about 30,000 U of the rHuPH20.

In some embodiments, the drug product comprises about 1,800 mg of the anti-CD38 antibody and about 45,000 U of the rHuPH20.

In some embodiments, the drug product comprises about 1,600 mg of the anti-CD38 antibody and about 30,000 U of the rHuPH20.

In some embodiments, the drug product comprises about 1,600 mg of the anti-CD38 antibody and about 45,000 U of the rHuPH20.

In some embodiments, the rHuPH20 is rHuPH20 having the amino acid sequence of SEQ ID NO: 22.

rHuPH20 is a recombinant rHuPH20 (HYLENEX® recombinant) and is described in Int. Pat. Publ. No. WO2004/078140. rHuPH20 is an enzyme that degrades hyaluronic acid (EC 3.2.1.35) and lowers the viscosity of hyaluronan in the extracellular matrix, thereby increasing tissue permeability. Enzymatic activity of rHuPH20, including rHuPH20 can be defined by units per mL (U/mL) or by total enzyme activity in a particular formulation (U). The standard definition for one unit (U) of enzyme activity is the amount of enzyme that catalyzes the reaction of 1 nmol of substrate per minute.

In some embodiments, the drug product comprises about 120 mg/mL of the anti-CD38 antibody and about 30,000 U of rHuPH20.

In some embodiments, the drug product comprises histidine at a concentration of from about 1 mM to about 50 mM.

In some embodiments, the drug product comprises histidine at a concentration of from about 5 mM to about 50 mM.

In some embodiments, the drug product comprises histidine at a concentration of from about 5 mM to about 30 mM.

In some embodiments, the drug product comprises histidine at a concentration of from about 5 mM to about 20 mM.

In some embodiments, the drug product comprises histidine at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM or about 50 mM.

In some embodiments, the drug product comprises sorbitol at a concentration of from about 50 mM to about 500 mM.

In some embodiments, the drug product comprises sorbitol at a concentration of from about 50 mM to about 450 mM.

In some embodiments, the drug product comprises sorbitol at a concentration of from about 50 mM to about 400 mM.

In some embodiments, the drug product comprises sorbitol at a concentration of from about 50 mM to about 350 mM.

In some embodiments, the drug product comprises sorbitol at a concentration of from about 100 mM to about 350 mM.

In some embodiments, the drug product comprises sorbitol at a concentration of from about 100 mM to about 300 mM.

In some embodiments, the drug product comprises sorbitol at a concentration of about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM or about 500 mM.

In some embodiments, the drug product comprises polysorbate-20 (PS-20) at a concentration of from about 0.01% w/v to about 0.1% w/v.

In some embodiments, the drug product comprises polysorbate-20 (PS-20) at a concentration of from about 0.01% w/v to about 0.08% w/v.

In some embodiments, the drug product comprises polysorbate-20 (PS-20) at a concentration of from about 0.01% w/v to about 0.04% w/v.

In some embodiments, the drug product comprises polysorbate-20 (PS-20) at a concentration of about 0.01% w/v, 0.02% w/v, 0.03% w/v, 0.04% w/v, 0.05% w/v, 0.06% w/v, 0.07% w/v, 0.08% w/v, 0.09% w/v or 0.1% w/v.

In some embodiments, the drug product comprises methionine at a concentration of from about 0.1 mg/mL to about 5 mg/mL.

In some embodiments, the drug product comprises methionine at a concentration of from about 0.1 mg/mL to about 2.5 mg/mL.

In some embodiments, the drug product comprises methionine at a concentration of from about 1 mg/mL to about 2 mg/mL.

In some embodiments, the drug product comprises methionine at a concentration of about 0.5 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1/7 mg/mL, about 1.8 mg/mL, about 1.9 mg/mL, about 2.0 mg/mL, about 2.1 mg/mL, about 2.2 mg/mL, about 2/3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.5 mg/mL, about 4 mg/mL, about 4.5 mg/mL or about 5 mg/mL.

In some embodiments, the drug product is at pH 5.0 to 6.0.

In some embodiments, the drug product is at pH 5.3 to 5.8.

In some embodiments, the drug product is at pH 5.5.

In some embodiments, the drug product is at pH 5.6.

In some embodiments, the drug product comprises histidine at a concentration of from about 5 mM to about 15 mM, sorbitol at a concentration of from about 100 mM to about 300 mM, polysorbate 20 (PS-20) at a concentration of from about 0.01% w/v to about 0.04% w/v; and methionine at a concentration of from about 1 mg/mL to about 2 mg/mL, at a pH of about 5.5.

In some embodiments, the drug product comprises about 100 mg/mL of the anti-CD38 antibody comprising the VH and the VL of SEQ ID NOs: 4 and 5, respectively, about 500 U/mL rHuPH20, about 10 mM histidine, about 300 mM sorbitol, about 0.04% w/v PS-20 and about 2 mg/mL methionine; at pH about 5.5.

In some embodiments, the drug product comprises about 120 mg/mL of the anti-CD38 antibody comprising the VH and the VL of SEQ ID NOs: 4 and 5, respectively, about 2,000 U/mL rHuPH20, about 10 mM histidine, about 300 mM sorbitol, about 0.04% w/v PS-20 and about 1 mg/mL methionine; at pH about 5.6.

In some embodiments, the drug product comprises about 100 mg/mL of the anti-CD38 antibody comprising the VH and the VL of SEQ ID NOs: 4 and 5, respectively, about 500 U/mL rHuPH20, about 10 mM histidine, about 300 mM sorbitol and about 2 mg/mL methionine; at pH about 5.5.

In some embodiments, the drug product comprises about 100 mg/mL of the anti-CD38 antibody comprising the VH and the VL of SEQ ID NOs: 4 and 5, respectively, about 500 U/mL rHuPH20, about 10 mM histidine, about 300 mM sorbitol, about 0.01% w/v PS-20 and about 2 mg/mL methionine; at pH about 5.5.

In some embodiments, the drug product comprises about 100 mg/mL of the anti-CD38 antibody comprising the VH and the VL of SEQ ID NOs: 4 and 5, respectively, about 500 U/mL rHuPH20, about 10 mM histidine, about 300 mM sorbitol, about 0.02% w/v PS-20 and about 2 mg/mL methionine; at pH about 5.5.

In some embodiments, the drug product comprises about 100 mg/mL of the anti-CD38 antibody comprising the VH and the VL of SEQ ID NOs: 4 and 5, respectively, about 500 U/mL rHuPH20, about 10 mM histidine, about 300 mM sorbitol, about 0.06% w/v PS-20 and about 2 mg/mL methionine; at pH about 5.5.

In some embodiments, the drug product comprises about 100 mg/mL of the anti-CD38 antibody comprising the VH and the VL of SEQ ID NOs: 4 and 5, respectively, about 50 U/mL rHuPH20, about 10 mM histidine, about 300 mM sorbitol, about 0.04% w/v PS-20 and about 1 mg/mL methionine; at pH about 5.5.

In some embodiments, the drug product comprises about 100 mg/mL of the anti-CD38 antibody comprising the VH and the VL of SEQ ID NOs: 4 and 5, respectively, about 500 U/mL rHuPH20, about 10 mM histidine, about 300 mM sorbitol, about 0.04% w/v PS-20 and about 1 mg/mL methionine; at pH about 5.5.

In some embodiments, the drug product comprises about 100 mg/mL of the anti-CD38 antibody comprising the VH and the VL of SEQ ID NOs: 4 and 5, respectively, about 2,000 U/mL rHuPH20, about 10 mM histidine, about 300 mM sorbitol, about 0.04% w/v PS-20 and about 1 mg/mL methionine; at pH about 5.5.

In some embodiments, the drug product comprises about 100 mg/mL of the anti-CD38 antibody comprising the VH and the VL of SEQ ID NOs: 4 and 5, respectively, about 5,000 U/mL rHuPH20, about 10 mM histidine, about 300 mM sorbitol, about 0.04% w/v PS-20 and about 1 mg/mL methionine; at pH about 5.5.

The disclosure also provides a drug product comprising a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising: culturing a CHO cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in a culture medium comprising about 8.0 ppb or less Mn.

The disclosure also provides a drug product comprising a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising: preparing a culture medium comprising about 8.0 ppb or less Mn; and culturing a host cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in culture medium comprising about 8.0 ppb or less Mn.

The disclosure also provides a drug product comprising a drug substance comprising an anti-CD38 antibody comprising a VH of SEQ ID NO: 7 and a VL of SEQ ID NO: 8 and having a G1F oligosaccharide content between about 15% and 27%, wherein the drug substance is manufactured using the process comprising: culturing a CHO cell transfected with a polynucleotide encoding the VH of SEQ ID NO: 7 and the VL of SEQ ID NO: 8 in a culture medium comprising about 8.0 parts per billion (ppb) or less Mn, thereby producing the drug substance.

The disclosure also provides a drug product comprising a drug substance comprising an anti-CD38 antibody comprising a VH of SEQ ID NO: 7 and a VL of SEQ ID NO: 8 and having a G1F oligosaccharide content between about 15% and 27%, wherein the drug substance is manufactured using the process comprising: preparing a culture medium comprising about 8.0 ppb or less Mn; and culturing a host cell transfected with a polynucleotide encoding the VH of SEQ ID NO: 7 and the VL of SEQ ID NO: 8 in culture medium comprising about 8.0 ppb or less manganese (Mn), thereby producing the drug substance.

The disclosure also provides a drug product comprising a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising: culturing a CHO cell transfected with a polynucleotide encoding the HC of SEQ ID NO: 9 and the LC of SEQ ID NO: 10 in a culture medium comprising about 8.0 parts per billion (ppb) or less manganese (Mn), thereby producing the drug substance.

The disclosure also provides a drug product comprising a drug substance comprising an anti-CD38 antibody comprising a HC of SEQ ID NO: 9 and a LC of SEQ ID NO: 10, respectively, and having a G1F oligosaccharide content between about 15% and 27%, wherein the drug substance is manufactured using the process comprising: preparing a culture medium comprising about 8.0 ppb or less Mn; and culturing a host cell transfected with a polynucleotide encoding the HC of SEQ ID NO: 9 and the LC of SEQ ID NO: 10, respectively, in culture medium comprising about 8.0 ppb or less manganese (Mn), thereby producing the drug substance.

The disclosure also provides a drug product comprising a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising culturing a CHO cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in a culture medium comprising about 6.5 ppb or less Mn, thereby producing the drug substance.

The disclosure also provides a drug product comprising a drug substance comprising an anti-CD38 antibody comprising a HCDR1, a HCDR2, a HCDR3, a LCDR1, a LCDR2 and a LCDR3 of SEQ ID NOs: 1, 2, 3, 4, 5, and 6, respectively, and having a G1F oligosaccharide content between about 15% and 27%, wherein the drug substance is manufactured using the process comprising preparing a culture medium comprising about 6.5 ppb or less Mn; and culturing a host cell transfected with a polynucleotide encoding the HCDR1, the HCDR2, the HCDR3, the LCDR1, the LCDR2 and the LCDR3 of SEQ ID NOs: 1, 2, 3, 4, 5, and 6, respectively, in culture medium comprising about 6.5 ppb or less Mn, thereby producing the drug product.

The disclosure also provides a drug product comprising a drug substance comprising an anti-CD38 antibody comprising a VH of SEQ ID NO: 7 and a VL of SEQ ID NO: 8 and having a G1F oligosaccharide content between about 15% and 27%, wherein the drug substance is manufactured using the process comprising culturing a CHO cell transfected with a polynucleotide encoding the VH of SEQ ID NO: 7 and the VL of SEQ ID NO: 8 in a culture medium comprising about 6.5 ppb or less Mn, thereby producing the drug substance.

The disclosure also provides a drug product comprising a drug substance comprising an anti-CD38 antibody comprising a VH of SEQ ID NO: 7 and a VL of SEQ ID NO: 8 and having a G1F oligosaccharide content between about 15% and 27%, wherein the drug substance is manufactured using the process comprising: preparing a culture medium comprising about 6.5 ppb or less Mn; and culturing a host cell transfected with a polynucleotide encoding the VH of SEQ ID NO: 7 and the VL of SEQ ID NO: 8 in culture medium comprising about 6.5 ppb or less Mn, thereby producing the drug substance.

The disclosure also provides a drug product comprising a drug substance comprising an anti-CD38 antibody comprising a HC of SEQ ID NO: 9 and a LC of SEQ ID NO: 10 and having a G1F oligosaccharide content between about 15% and 27%, wherein the drug substance is manufactured using the process comprising culturing a CHO cell transfected with a polynucleotide encoding the HC of SEQ ID NO: 9 and the LC of SEQ ID NO: 10 in a culture medium comprising about 6.5 parts per billion (ppb) or less manganese (Mn), thereby producing the drug substance.

The disclosure also provides a drug product comprising a drug substance comprising an anti-CD38 antibody comprising a HC of SEQ ID NO: 9 and a LC of SEQ ID NO: 10, respectively, and having a G1F oligosaccharide content between about 15% and 27%, wherein the drug substance is manufactured using the process comprising preparing a culture medium comprising about 6.5 ppb or less Mn; and culturing a host cell transfected with a polynucleotide encoding the HC of SEQ ID NO: 9 and the LC of SEQ ID NO: 10, respectively, in culture medium comprising about 6.5 ppb or less manganese (Mn), thereby producing the drug substance.

In some embodiments, the drug product of the disclosure described herein comprising about 20 mg/ml of the anti-CD38 antibody comprising the HCDR1, the HCDR2, the HCDR3, the LCDR1, the LCDR2 and the LCDR3 of SEQ ID NOs: 1, 2, 3, 4, 5, and 6, respectively, the VH of SEQ ID NO: 7 and the VL of SEQ ID NO: 8 and/or the HC of SEQ ID NO: 9 and the LC of SEQ ID NO: 10 is formulated in about 25 mM acetic acid, about 60 mM sodium chloride, about 140 mM mannitol and about 0.04% w/v polysorbate-20 (PS-20); at pH about 5.5.

In some embodiments, the drug product of the disclosure described herein comprises from about 20 mg/mL to about 180 mg/mL of the anti-CD38 antibody comprising the HCDR1, the HCDR2, the HCDR3, the LCDR1, the LCDR2 and the LCDR3 of SEQ ID NOs: 1, 2, 3, 4, 5, and 6, respectively, the VH of SEQ ID NO: 7 and the VL of SEQ ID NO: 8 and/or the HC of SEQ ID NO: 9 and the LC of SEQ ID NO: 10 and recombinant human hyaluronidase (rHuPH20) in an amount of from about 30,000 U to about 45,000 U.

rHuPH20 is a recombinant human hyaluronidase comprising the amino acid sequence of SEQ ID NO: 15.

```
SEQ ID NO: 15:
MGVLKFKHIFFRSFVKSSGVSQIVFTFLLIPCCLTLNFRAPPVIPNVP

FLWAWNAPSEFCLGKFDEPLDMSLFSFIGSPRINATGQGVTIFYVDRL

GYYPYIDSITGVTVNGGIPQKISLQDHLDKAKKDITFYMPVDNLGMAV

IDWEEWRPTWARNWKPKDVYKNRSIELVQQQNVQLSLTEATEKAKQEF

EKAGKDFLVETIKLGKLLRPNHLWGYYLFPDCYNHHYKKPGYNGSCFN

VEIKRNDDLSWLWNESTALYPSIYLNTQQSPVAATLYVRNRVREAIRV

SKIPDAKSPLPVFAYTRIVFTDQVLKFLSQDELVYTFGETVALGASGI

VIWGTLSIMRSMKSCLLLDNYMETILNPYIINVTLAAKMCSQVLCQEQ

GVCIRKNWNSSDYLHLNPDNFAIQLEKGGKFTVRGKPTLEDLEQFSEK

FYCSCYSTLSCKEKADVKDTDAVDVCIADGVCIDAFLKPPMETEEPQI

FYNASPSTLSATMFIVSILFLIISSVASL
```

In some embodiments, the drug product of the disclosure described herein comprises from about 20 mg/mL to about 180 mg/mL of the anti-CD38 antibody comprising the HCDR1, the HCDR2, the HCDR3, the LCDR1, the LCDR2 and the LCDR3 of SEQ ID NOs: 1, 2, 3, 4, 5, and 6, respectively, the VH of SEQ ID NO: 7 and the VL of SEQ ID NO: 8 and/or the HC of SEQ ID NO: 9 and the LC of SEQ ID NO: 10, recombinant human hyaluronidase (rHuPH20) in an amount of from about 30,000 U to about 45,000 U, histidine at a concentration of from about 5 mM to about 15 mM, sorbitol at a concentration of from about 100 mM to about 300 mM, PS-20 at a concentration of from about 0.01% w/v to about 0.04% w/v; and methionine at a concentration of from about 1 mg/mL to about 2 mg/mL, at a pH of about 5.5.

In some embodiments, the drug product of the disclosure described herein comprises about 120 mg/mL of the anti- CD38 antibody comprising the HCDR1, the HCDR2, the HCDR3, the LCDR1, the LCDR2 and the LCDR3 of SEQ ID NOs: 1, 2, 3, 4, 5, and 6, respectively, the VH of SEQ ID NO: 7 and the VL of SEQ ID NO: 8 and/or the HC of SEQ ID NO: 9 and the LC of SEQ ID NO: 10, about 10 mM Histidine, about 300 mM Sorbitol, about 1 mg/mL methionine, about 0.04% Polysorbate 20, and about 2000 U/ml rHuPH20, pH 5.6.

In some embodiments, the drug product is DARZALEX® (daratumumab).

In some embodiments, the drug product is a biosimilar of DARZALEX® (daratumumab).

Method of Treatment

The disclosure also provides a method of treating multiple myeloma in a subject who has received at least three prior lines of therapy including a proteasome inhibitor (PI) and an immunomodulatory agent or who is double-refractory to the PI and the immunomodulatory agent, comprising administering to the subject a therapeutically effective amount of the drug product of the disclosure.

Exemplary proteasome inhibitors include VELCADE® (bortezomib), carfilzomib, or ixazomib. In some embodiments, the proteasome inhibitor is bortezomib. Exemplary immunomodulatory agents include cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In some embodiments, the drug product is administered according to the drug product label.

The disclosure also provides a method of treating multiple myeloma in a subject who has received at least two prior therapies including lenalidomide and proteasome inhibitor, comprising administering to the subject a therapeutically effective amount of the drug product of the disclosure in combination with a therapeutically effective amount of pomalidomide and dexamethasone. In some embodiments, the drug product, pomalidomide and dexamethasone are administered at dosages indicated in the drug product label.

The disclosure also provides a method of treating multiple myeloma in a subject who has received at least one prior therapy, comprising administering to the subject a therapeutically effective amount of the drug product of the disclosure in combination with a therapeutically effective amount of lenalidomide and dexamethasone. In some embodiments, the drug product, lenalidomide and dexamethasone are administered at dosages indicated in the drug product label.

The disclosure also provides a method of treating multiple myeloma in a subject who has received at least one prior therapy, comprising administering to the subject a therapeutically effective amount of the drug product of the disclosure in combination with a therapeutically effective amount of bortezomib and dexamethasone. In some embodiments, the drug product, bortezomib and dexamethasone are administered at dosages indicated in the drug product label.

The disclosure also provides a method of treating multiple myeloma in a subject who is ineligible for autologous stem cell transplant, comprising administering to the subject a therapeutically effective amount of the drug product of the disclosure in combination with a therapeutically effective amount of bortezomib, melphalan and prednisone. In some embodiments, the drug product, bortezomib, melphalan and prednisone are administered at dosages indicated in the drug product label.

The disclosure also provides a method of treating multiple myeloma in a subject who is ineligible for autologous stem cell transplant, comprising administering to the subject a therapeutically effective amount of the drug product of the disclosure in combination with a therapeutically effective amount of lenalidomide and dexamethasone. In some embodiments, lenalidomide and dexamethasone are administered at dosages indicated in the drug product label.

The disclosure also provides a method of treating multiple myeloma in a subject who has received at least one prior therapy, comprising administering to the subject a therapeutically effective amount of the drug product of the disclosure in combination with a therapeutically effective amount of lenalidomide and dexamethasone. In some embodiments, the drug product, lenalidomide and dexamethasone are administered at dosages indicated in the drug product label.

In some embodiments, the drug product is administered at a dose of 16 mg/kg once a week during weeks 1-6, once in three weeks during weeks 7-54 and once in four weeks thereafter.

In some embodiments, the drug product is administered at a dose of 16 mg/kg once a week during weeks 1-8, once in two weeks during weeks 9-24 and once in four weeks thereafter.

In some embodiments, the drug product is administered at a dose of 16 mg/kg once a week during weeks 1-9, once in three weeks during weeks 10-24 and once in four weeks thereafter.

In some embodiments, pomalidomide is administered 4 mg once daily orally on days 1-21 of repeated 28-day cycles and dexamethasone is administered 20 mg or 40 mg once a week intravenously.

In some embodiments, lenalidomide is administered 25 mg once daily orally on days 1-21 of repeated 28-day cycles and dexamethasone is administered 20 mg or 40 mg once a week intravenously.

In some embodiments, bortezomib is administered by subcutaneous (SC) injection or intravenous (IV) infusion at a dose of 1.3 mg/m² body surface area twice weekly for two weeks (days 1, 4, 8, and 11) of repeated 21 day treatment cycles for a total of 8 cycles and dexamethasone is administered 20 mg orally on days 1, 2, 4, 5, 8, 9, 11, and 12 of each of the 8 bortezomib cycles.

In some embodiments, bortezomib is administered by subcutaneous (SC) injection at a dose of 1.3 mg/m² body surface area twice weekly at weeks 1, 2, 4 and 5 for the first 6-week cycle (cycle 1; 8 doses), followed by once weekly administrations at weeks 1, 2, 4 and 5 for eight more 6-week cycles (cycles 2-9; 4 doses per cycle), melphalan is administered at 9 mg/m² on days 1 to 4 of the nine 6-week cycles (cycles 1-9) and prednisone is administered orally at 60 mg/m² on days 1 to 4 of the nine 6-week cycles (cycles 1-9).

The disclosure also provides a method of treating CD38-positive hematological malignancy in a subject, comprising administering to the subject a therapeutically effective amount of the drug product of the disclosure.

In some embodiments, the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL), light chain amyloidosis, myelogenous leukemia (AML), Waldenström's macroglobulinemia, smoldering multiple myeloma (SMM), monoclonal gammopathy of unknown significance (MGUS), membranoproliferative glomurelonephritis, chronic lymphocytic leukemia (CLL) or Burkitt's lymphoma.

Examples of B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

The disclosure also provides a method of inhibiting growth and/or proliferation of a cell expressing CD38, comprising administering to the subject the drug product of the disclosure described herein.

In some embodiments, the cell expressing CD38 is a B cell, a plasma cell, a monocyte or a T cell. In some embodiments, the cell expressing CD38 is involved in pathogenesis of a tumor or an immune disorder. In some embodiments, the immune disorder is an autoimmune disorder. In some embodiments, the immune disorder is psoriasis, psoriatic arthritis, dermatitis, systemic scleroderma, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, multiple sclerosis, HIV, and herpes virus associated diseases.

The disclosure also provides a method of treating an autoimmune disorder in a subject, comprising administering to a subject a therapeutically effective amount of the drug product of the disclosure described herein.

In some embodiments, the autoimmune disorder is systemic lupus erythematosus, Sjögren's syndrome or rheumatoid arthritis (RA).

While having described the disclosure in general terms, the embodiments of the disclosure will be further disclosed in the following examples that should not be construed as limiting the scope of the claims.

Example 1. Manufacturing Investigation

During manufacturing of DARZALEX® (daratumumab), some lots were identified to fall out of specification (OOS) or out of trend (OOT) in terms of DARZALEX® (daratumumab), G1F % profile. Investigations were initiated to identify root cause and especially the role of trace metal impurities such as manganese (Mn) associated with the raw materials to the modulation of the glycan profile in DARZALEX® (daratumumab).

The raw material characterization study was designed to evaluate concentration of Mn in Dry powder medium (DPM) raw materials and hydrated media solutions associated with DARZALEX® (daratumumab) manufacturing batches. DARZALEX® (daratumumab) active substance was manufactured in an 11-stage process consisting of fed batch cell culture followed by purification with a series of chromatography, viral inactivation and filtration steps. The amount of Mn in raw materials were assessed using ICP-MS with pre-digestion of both DPM and hydrated media samples using nitric acid and peroxide. DARZALEX® (daratumumab) samples were tested for the relative amounts of G0F % and G1F % at viral inactivation and neutralization (VIN) or at drug substance (DS) stage.

Mn concentration in DPM was used as a predictive tool to estimate the expected Mn concentration in hydrated media based on the cumulative contribution of Mn in the key DPM components. Production bioreactor concentration was calculated based on the mass added per liter for the basal and feed medias, followed by an adjusted concentration based on the basal Mn concentration plus the adjusted feed according to the feed rate.

Manganese concentration in hydrated media: Predicted Mn Solution(μg/L~ppb)=[(Component 1(g/L)*Mn1(ppb))+(Component 2(g/L)*Mn2 (ppb))+ . . . (Component $n$(g/L)*Mn $n$ (ppb))]1/1000 Manganese concentration in bioreactor:(μg/L~ppb)=Basal Mn(ppb)+(Feed Mn(ppb)*Feed Factor).

Hydration of the DPM resulted in significant dilution of manganese concentrations in the final liquid media. As a result of this dilution, the Mn concentrations in the hydrated media components were not within the quantitative range of the ICP-MS assay. Results, however, were used for overall understanding and confirmation of the general qualitative relationship of Mn concentration and glycosylation and for the DPM model. Variations in these measurements of the hydrated media were expected to be greater than for the DPM measurements (which were within quantitative range).

Figure 2:
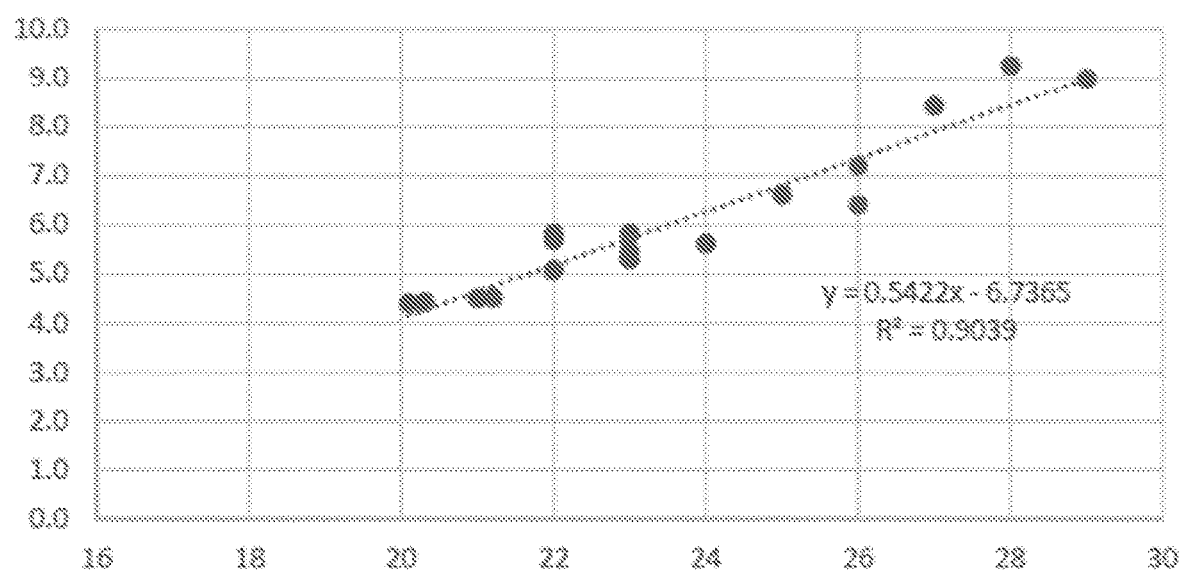
FIG. 2 shows the correlation of DARZALEX® (daratumumab) percentage of G1F oligosaccharides (G1F %) vs. DPM calculated Mn concentration in various manufacturing batches. Y-axis: Mn concentration (ppb); X-axis: G1F %.

ICP-MS data for the DPM components and DARZALEX® (daratumumab) G0F % and G1F % for twelve manufacturing batches were obtained. Table 1 shows the percent G0F, G1F, and manganese total concentration and concentration in basal and feed medias in the various batches. The data demonstrated that Mn concentration about 6.6 ppb and below resulted in DARZALEX® (daratumumab) in-specification glycosylation pattern. The correlation between Mn DPM concentration and DARZALEX® (daratumumab) percentage G0F and percentage G1F are shown in FIG. 1 and FIG. 2, respectively in various analyzed batches. The results demonstrated a correlation of $R^2$=0.904 and $R^2$=0.939, respectively. The batches in FIG. 1 and FIG. 2 are not necessarily the same as those shown in Table 1.

Figure 3:
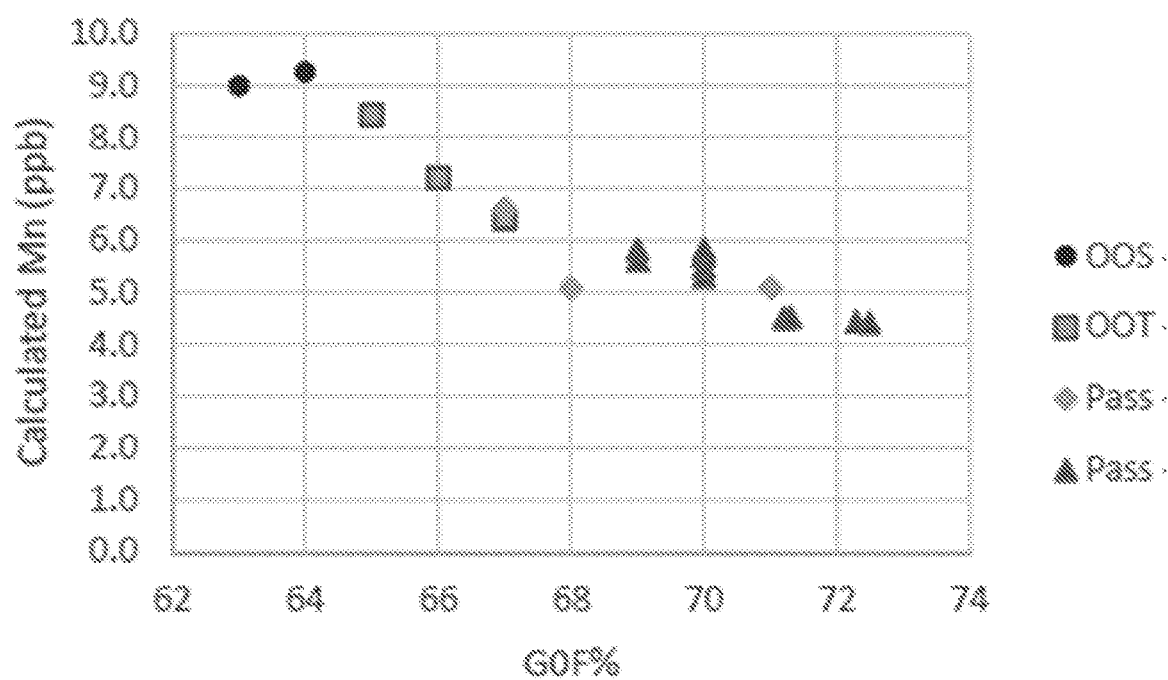
FIG. 3 shows DARZALEX® (daratumumab) G0F % vs. Mn concentration calculated from DPM bioreactor media components for out of specification (OOS), out of trend (OOT) and passed batches.
Figure 4:
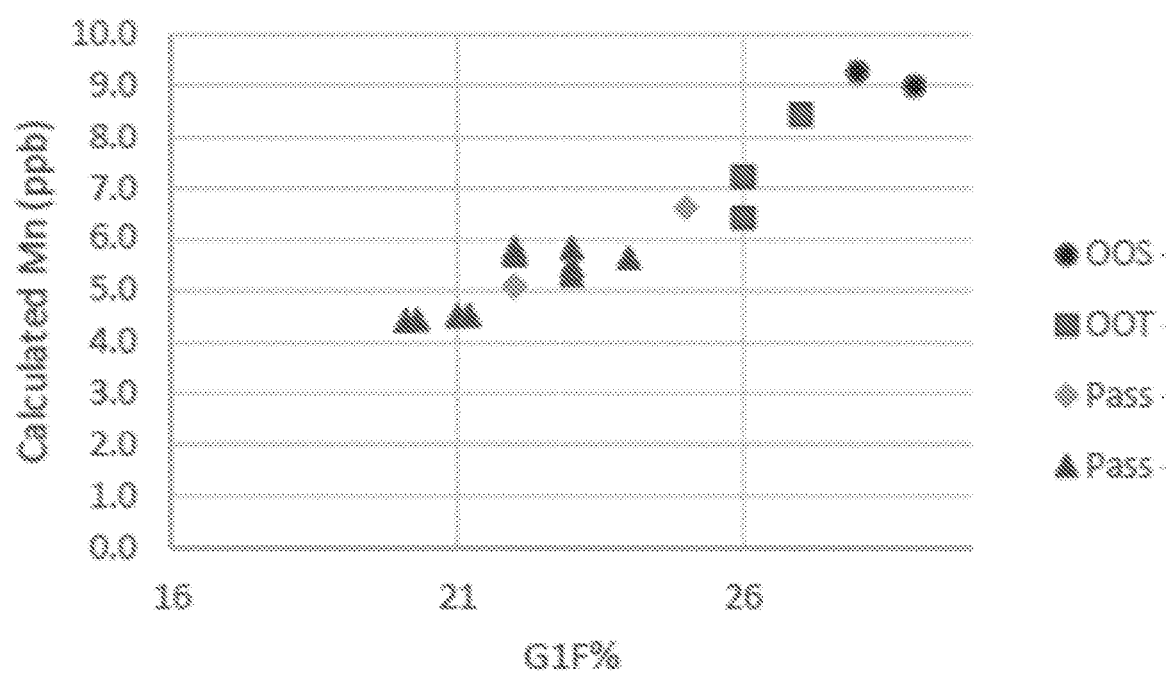
FIG. 4 shows DARZALEX® (daratumumab) G1F % vs. Mn concentration calculated from DPM bioreactor media components for OOS, OOT and passed batches.

FIG. 3 shows the calculated Mn DPM concentration and DARZALEX® (daratumumab) G0F % in OOS, OOT and passed batches. FIG. 4 shows the calculated Mn DPM concentration and DARZALEX® (daratumumab) G1F % in OOS, OOT and passed batches.

TABLE 1

| Lot | G0F (%) | G1F (%) | Basal media Mn (ppb) | Feed media Mn (ppb) | Total Mn (ppb) | Summary results |
|---|---|---|---|---|---|---|
| 16C0922 | 63 | 29 | 7.7 | 23.8 | 9 | OOS |
| 16C0918 | 64 | 28 | 7.9 | 25.1 | 9.3 | OOS |
| 16C0927 | 65 | 27 | 7.2 | 22.8 | 8.4 | OOT (on spec) |
| 16C0913 | 66 | 26 | 6.2 | 18.9 | 7.2 | Pass (CPV OOT) |
| 16C0942 | 67 | 26 | 5.8 | 11.5 | 6.4 | Pass (CPV OOT) |
| 16C0943 | 67 | 25 | 5.9 | 13.4 | 6.6 | Pass |
| 16C0917 | 68 | 22 | 4.4 | 12.5 | 5.1 | Pass |
| 16C0928 | 71 | 22 | 3.7 | 25.7 | 5.1 | Pass |
| L17C0901 | 71 | 21 | 3.9 | 11.5 | 4.5 | Pass |
| L17C0902 | 71 | 21 | 3.9 | 11.5 | 4.5 | Pass |
| L17C0903 | 72 | 20 | 3.8 | 11.3 | 4.4 | Pass |
| L17C0904 | 73 | 20 | 3.8 | 11.3 | 4.4 | Pass |
| 3101737 | 70 | 23 | 5 | 5.4 | 5.3 | Pass |
| 3101738 | 70 | 23 | 5 | 5.4 | 5.3 | Pass |

TABLE 1-continued

| Lot | G0F (%) | G1F (%) | Basal media Mn (ppb) | Feed media Mn (ppb) | Total Mn (ppb) | Summary results |
|---|---|---|---|---|---|---|
| 3101739 | 70 | 23 | 5 | 8.2 | 5.5 | Pass |
| 3101741 | 69 | 23 | 5 | 10.4 | 5.8 | Pass |
| 3101742 | 69 | 24 | 5 | 10.4 | 5.6 | Pass |
| 3101743 | 70 | 22 | 5.1 | 10.4 | 5.7 | Pass |
| 3101744 | 70 | 22 | 5.1 | 10.4 | 5.7 | Pass |
| 3101745 | 70 | 22 | 5.2 | 10.5 | 5.8 | Pass |

Figure 5:
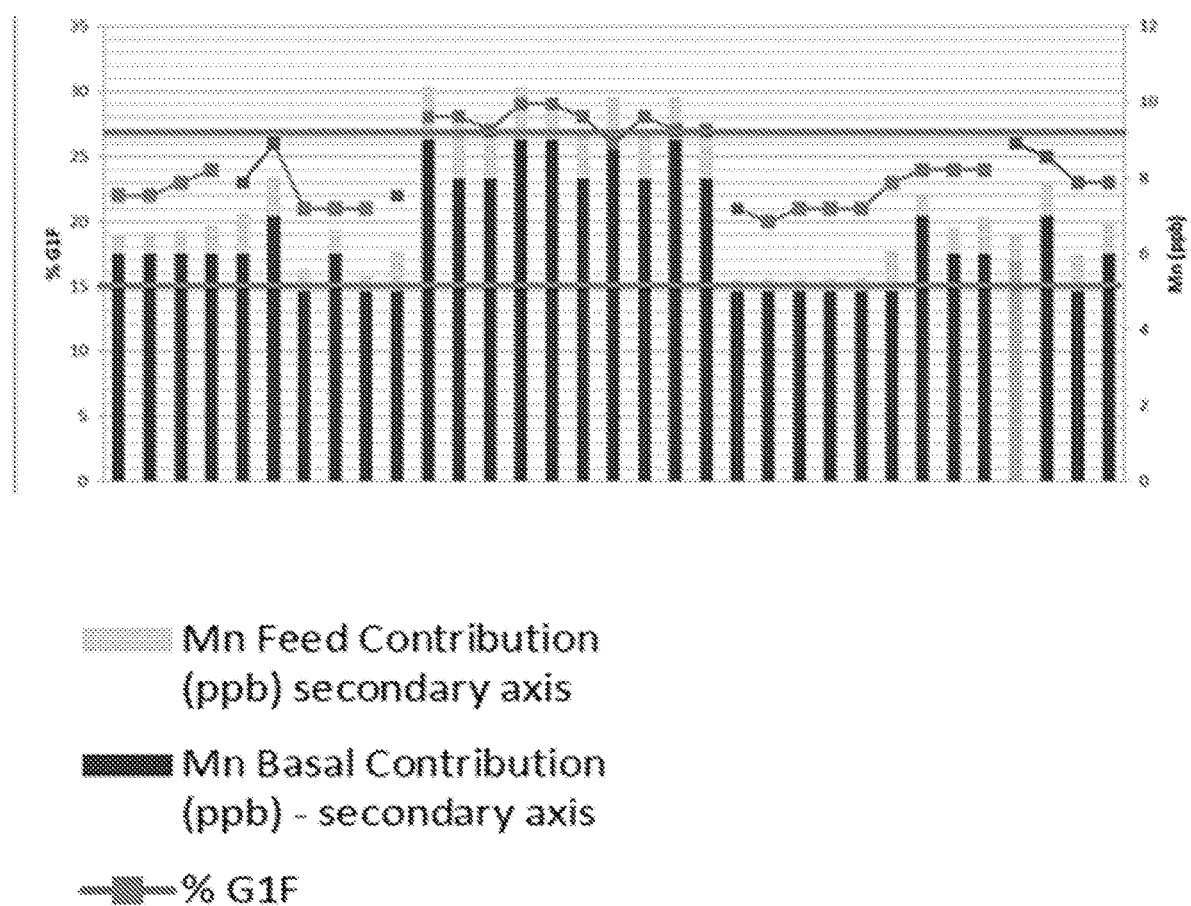
FIG. 5 shows DARZALEX® (daratumumab) G1F % (indicated as % G1F in the figure) and Mn concentration in various production batches over time.

Mn values calculated from DPM measurements.
OOS: out of specification;
OOT: out of trend:
CPV:

FIG. 5 shows the % G1F of DARZALEX® (daratumumab) within manufacturing batches over time and the Mn concentration contributed by basal or by feed media in each batch. Based on these data, it appeared that when the total contribution of Mn was greater than ~8.5 ppb (secondary y-axis) the % G1F was OOT/OOS (≥26%—primary y-axis). When the total contribution of Mn was below ~6.5 ppb, % G1F was always passing and within trend. Mn concentration between about 2 ppb and 8 ppb resulted in n DARZALEX® (daratumumab) with % G1F content between about 15% and 27%.

Figure 6:
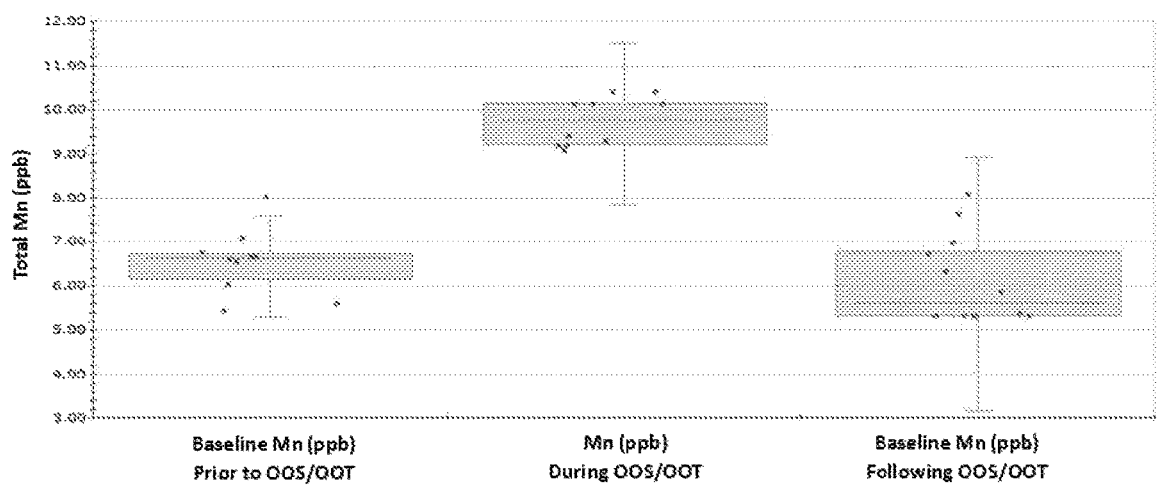
FIG. 6 shows the total Mn concentration (ppb) prior, during and following OOS/OOT batch manufacturing.

Analysis into the root cause of OOS/OOT lots, a trace metal process control strategy was established which included pre-screening of media components for manganese and subsequent monitoring and/or blending of the various medias. The process control strategy was successful in eliminating DARZALEX® (daratumumab) OOS/OOT batches. FIG. 6 shows the total Mn concentration (ppb) prior, during and following OOS/OOT batch manufacturing. Mn concentration in the OOT/OOS batches were in the range of about 9-10.5 ppb whereas the batches prior or after OOT/OOS had Mn concentration between about 5-8 ppb.

Methods
Quantification of Oligosaccharide Composition

DARZALEX® (daratumumab) oligosaccharide composition was determined using standard methods.

Inductively Coupled Plasma Mass Spectrometry (ICP-MS)

ICP-MS was used to quantitate at parts per billion (ppb, µg/liter) trace metal concentrations in the chemically defined media used to produce different antibody batches. In brief, the method consisted of an acid digestion procedure to digest carbon rich sources to carbon dioxide and water before the sample was injected into an ICP-MS instrument such as the NexION® 350X ICP-MS (PerkinElmer). The wet chemical digestions utilized different acids and oxidizing agents. Preferred combinations included nitric acid ($HNO_3$), hydrogen peroxide ($H_2O_2$), and hydrochloric acid (HCl).

A digestion method was specifically developed for use in determining metal concentrations in chemically defined media that could be adapted to dry media powder or hydrated media samples (1 g sample=1 mL hydrated sample).

Digestion Method

- ~1 g dry samples (±0.5 g, weight recorded to 0.001 g) or ~1 mL solution samples (±0.5 mL, weight recorded to 0.001 g) were added to digestion vessels (applicable spike solutions are also added at this time)
- 5.0 mL of 50% v/v $HNO_3$ (nitric acid) and 2.5 mL concentrated $H_2O_2$ were added to samples and digestion vessels are then capped immediately with polypropylene watch glasses—$H_2O_2$ was added slowly to avoid sample bubbling over
- samples were heated for 30 minutes at 95° C. (±5° C.)
- samples were removed from heat and allowed to cool
- 2.5 mL concentrated $HNO_3$ was added and samples were heated for 30 minutes at 95° C. (±5° C.). If brown fumes were generated, indicating oxidation of the sample by $HNO_3$, the step was repeated over and over until no brown fumes were given off by the sample. No brown fumes was an indication of complete oxidation by $HNO_3$.
- samples were removed from heat and allowed to cool
- 2.5 mL concentrated $HNO_3$ and 5 mL concentrated HCl were added and samples were heated for 2 hours at 95° C. (±5° C.)
- samples were removed from heat and allowed to cool
- total volume of samples was brought to 50 mL with deionized water (DIW) and then samples were ready for analysis All heating at 95° C. (±5° C.) was done in reflux, without boiling, with samples capped with polypropylene watch glasses, in pre-heated hot block (e.g., Hotblock®). Digestion vials were soaked in 5%/5% v/v $HNO_3$/HCl overnight and triple rinsed with DIW prior to use. Polypropylene watch glasses were soaked in 5%/5% v/v $HNO_3$/HCl overnight and triple rinsed with DIW prior to use. Plastic tips for pipetting are triple rinsed with reagent prior to use. Samples were analyzed by ICP-MS within 2 weeks of digestion. The methods can also be adapted to automated processes, for example using the Vulcan Automated Digestion and Work-Up System (Questron Technologies Corp.)

Reagents and Standards used: deionized water (DIW) tested to be free of metals, >18.0 MΩ; trace metals spike standards from NIST traceable sources; concentrated $HNO_3$, reagent grade or higher, tested for metals; 50% $HNO_3$ solution—500 mL DIW and slowly added 500 mL $HNO_3$, solution can be kept for 6 months; concentrated HCl, reagent grade or higher, tested for metals; concentrated (30% v/v) $H_2O_2$, all DIW, $HNO_3$, and HCL are tested regularly to ensure there is no contamination.

We claim:

1. A method of producing an anti-CD38 antibody expressed from a polynucleotide encoding a heavy chain variable region (VH) of SEQ ID NO: 7 and a light chain variable region (VL) of SEQ ID NO: 8 having an asialo, mono-galacto core-fucosylated biantennary glycan (G1F) oligosaccharide content between 15% and 27%, comprising:
   a) preparing a culture medium comprising between 2 parts per billion (ppb) and 8.5 manganese (Mn); and
   b) controlling the G1F oligosaccharide content of the anti-CD38 antibody by culturing a host cell comprising the polynucleotide encoding the VH of SEQ ID NO: 7 and the VL of SEQ ID NO: 8 in the culture medium prepared in step a), thereby producing the anti-CD38 antibody expressed from the polynucleotide encoding the VH of SEQ ID NO: 7 and the VL of SEQ ID NO: 8 having the G1F oligosaccharide content between 15% and 27%.

2. The method of claim 1, wherein the G1F oligosaccharide content of the anti-CD38 antibody is between 15% and 25%.

3. The method of claim 2, wherein the G1F oligosaccharide content of the anti-CD38 antibody is between 21% and 25%.

4. The method of claim 1, wherein an asialo, agalacto core-fucosylated biantennary glycan (G0F) oligosaccharide content of the anti-CD38 antibody is between 65% and 74%.

5. The method of claim 4, wherein the G0F oligosaccharide content of the anti-CD38 antibody is between 68% and 74%.

6. The method of claim 1, wherein preparing the culture medium comprises:
   measuring Mn concentration in one or more batches of raw material components,
   selecting those one or more batches of raw material components that in combination contain between 2 ppb and 8.5 ppb Mn, and
   using the selected one or more batches of raw material components to prepare the culture medium.

7. The method of claim 6, wherein the culture medium is prepared to comprise between 4.0 ppb and 8.5 ppb Mn.

8. The method of claim 7, wherein the culture medium is prepared to comprise between 4.0 ppb and 6.5 ppb Mn.

9. The method of claim 8, wherein the culture medium is prepared to comprise between 5.0 ppb and 6.5 ppb Mn.

10. The method of claim 1, wherein the G1F oligosaccharide content of the anti-CD38 antibody is between 15% and 27%, the G0F oligosaccharide content of the anti-CD38 antibody is between 65% and 74%, and the culture medium is prepared to comprise between 4.0 ppb and 8.5 ppb Mn.

11. The method of claim 1, wherein the G1F oligosaccharide content of the anti-CD38 antibody is between 15% and 25%, the G0F oligosaccharide content of the anti-CD38 antibody is between 68% and 74%, and the culture medium is prepared to comprise between 4.0 ppb and 6.5 ppb Mn.

12. The method of claim 11, wherein the G1F oligosaccharide content of the anti-CD38 antibody is between 21% and 25%, the G0F oligosaccharide content of the anti-CD38 antibody is between 68% and 74%, and the culture medium is prepared to comprise between 5.0 ppb and 6.5 ppb Mn.

13. The method of claim 1, wherein the culture medium is a basal medium or a feed medium.

14. The method of claim 13, wherein culturing comprises a fed-batch culture or a perfusion culture.

15. The method of claim 14, wherein the host cell is an eukaryotic cell.

16. The method of claim 15, wherein the eukaryotic cell is a CHO cell, a PER.C6 cell, a NS0 cell, a Sp2/0 cell or a BHK cell.

17. The method of claim 16, wherein the CHO cell is a CHO-K1 cell, a CHO-DG44 cell, a CHO-S cell or a CHO-DXB11 cell.

18. The method of claim 17, wherein the CHO cell is deficient in glutamine synthetase (GS).

19. The method of claim 1, wherein the method is conducted under good manufacturing practice (GMP) compliant conditions.

20. The method of claim 19, wherein the anti-CD38 antibody comprises the VH of SEQ ID NO: 7 and the VL of SEQ ID NO: 8.

21. The method of claim 20, wherein the anti-CD38 antibody comprises an IgG1 isotype.

22. The method of claim 21, wherein the anti-CD38 antibody comprises a heavy chain (HC) of SEQ ID NO: 9 and a light chain (LC) of SEQ ID NO: 10.

23. The method of claim 1, wherein the anti-CD38 antibody is a biosimilar.

24. The method of claim 1, wherein the culture medium is prepared to comprise between 2 ppb and 6.5 ppb Mn.

25. The method of claim 1, wherein the anti-CD38 antibody is daratumumab.

26. A method of producing an anti-CD38 antibody expressed from a polynucleotide encoding the VH of SEQ ID NO: 7 and a VL of SEQ ID NO: 8 having a G1F oligosaccharide content between 15% and 27%, comprising:
a) culturing a host cell expressing the polynucleotide encoding the VH of SEQ ID NO: 7 and the VL of SEQ ID NO: 8 in conditions that the anti-CD38 antibody is produced; and
b) controlling the G1F oligosaccharide content of the anti-CD38 antibody by monitoring the concentration of Mn in the culture medium during biosynthesis of the anti-CD38 antibody and regulating the concentration of Mn in the culture medium during biosynthesis of the anti-CD38 antibody, wherein the concentration of Mn in the culture medium is regulated to comprise between 2 ppb and 8.5 ppb Mn, thereby producing the anti-CD38 antibody having the G1F oligosaccharide content between 15% and 27%.

27. The method of claim 26, wherein the G1F oligosaccharide content of the anti-CD38 antibody is between 15% and 25%.

28. The method of claim 27, wherein the G1F oligosaccharide content of the anti-CD38 antibody is between 21% and 25%.

29. The method of claim 26, wherein a G0F oligosaccharide content of the anti-CD38 antibody is between 65% and 74%.

30. The method of claim 27, wherein the G0F oligosaccharide content of the anti-CD38 antibody is between 68% and 74%.

31. The method of claim 26, wherein the concentration of Mn in the culture medium is regulated to comprise between 4.0 ppb and 8.5 ppb Mn.

32. The method of claim 31, wherein the concentration of Mn in the culture medium is regulated to comprise between 4.0 ppb and 6.5 ppb Mn.

33. The method of claim 32, wherein the concentration of Mn in the culture medium is regulated to comprise between 5.0 ppb and 6.5 ppb Mn.

34. The method of claim 26, wherein the G1F oligosaccharide content of the anti-CD38 antibody is between 15% and 27%, the G0F oligosaccharide content of the anti-CD38 antibody is between 65% and 74%, and the culture medium is regulated to comprise between 4.0 ppb and 8.5 ppb Mn.

35. The method of claim 27, wherein the G1F oligosaccharide content of the anti-CD38 antibody is between 15% and 25%, the G0F oligosaccharide content of the anti-CD38 antibody is between 68% and 74%, and the culture medium is regulated to comprise between 4.0 ppb and 6.5 ppb Mn.

36. The method of claim 28, wherein the G1F oligosaccharide content of the anti-CD38 antibody is between 21% and 25%, the G0F oligosaccharide content of the anti-CD38 antibody is between 68% and 74%, and the culture medium is regulated to comprise between 5.0 ppb and 6.5 ppb Mn.

37. The method of claim 26, wherein the culture medium is a basal medium or a feed medium.

38. The method of claim 37, wherein culturing comprises a fed-batch culture or a perfusion culture.

39. The method of claim 38, wherein the host cell is an eukaryotic cell.

40. The method of claim 39, wherein the eukaryotic cell is a CHO cell, a PER.C6 cell, a NS0 cell, a Sp2/0 cell or a BHK cell.

41. The method of claim 40, wherein the CHO cell is a CHO-K1 cell, a CHO-DG44 cell, a CHO-S cell or a CHO-DXB11 cell.

42. The method of claim 41, wherein the CHO cell is deficient in GS.

43. The method of claim 26, wherein the method is conducted under GMP-compliant conditions.

44. The method of claim 43, wherein the anti-CD38 antibody comprises the VH of SEQ ID NO: 7 and the VL of SEQ ID NO: 8.

45. The method of claim 44, wherein the anti-CD38 antibody comprises an IgG1 isotype.

46. The method of claim 45, wherein the anti-CD38 antibody comprises the HC of SEQ ID NO: 9 and the LC of SEQ ID NO: 10.

47. The method of claim 26, wherein the anti-CD38 antibody is a biosimilar.

48. The method of claim 26, wherein the culture medium is regulated to comprise between 2 ppb and 6.5 ppb Mn.

49. The method of claim 26, wherein the anti-CD38 antibody is daratumumab.

50. A method of producing a drug product comprising an anti-CD38 antibody expressed from a polynucleotide encoding the VH of SEQ ID NO: 7 and the VL of SEQ ID NO: 8 and having a G1F oligosaccharide content between 15% and 27%, comprising:
a) preparing a culture medium comprising between 2 ppb and 8.5 ppb Mn;
b) controlling the G1F oligosaccharide content of the anti-CD38 antibody by culturing a host cell comprising the polynucleotide encoding the VH of SEQ ID NO: 7 and the VL of SEQ ID NO: 8 in the culture medium prepared in step a), thereby producing the anti-CD38 antibody having the G1F oligosaccharide content between 15% and 27%; and c) formulating the anti-CD38 antibody as a drug product.

51. The method of claim 50, wherein the G1F oligosaccharide content of the anti-CD38 antibody is between 15% and 25%.

52. The method of claim 51, wherein the G1F oligosaccharide content of the anti-CD38 antibody is between 21% and 25%.

53. The method of claim 50, wherein a G0F oligosaccharide content of the anti-CD38 antibody is between 65% and 74%.

54. The method of claim 53, wherein the G0F oligosaccharide content of the anti-CD38 antibody is between 68% and 74%.

55. The method of claim 50, wherein preparing the culture medium comprises:
   measuring Mn concentration in one or more batches of raw material components,
   selecting those one or more batches of raw material components that in combination contain between 2 ppb and 8.5 ppb Mn, and
   using the selected one or more batches of raw material components to prepare the culture medium.

56. The method of claim 50, wherein the culture medium is prepared to comprise between 4.0 ppb and 8.5 ppb Mn.

57. The method of claim 56, wherein the culture medium is prepared to comprise between 4.0 ppb and 6.5 ppb Mn.

58. The method of claim 57, wherein the culture medium is prepared to comprise between 5.0 ppb and 6.5 ppb Mn.

59. The method of claim 50, wherein the G1F oligosaccharide content of the anti-CD38 antibody is between 15% and 27%, the G0F oligosaccharide content of the anti-CD38 antibody is between 65% and 74%, and the culture medium is prepared to comprise between 4.0 ppb and 8.5 ppb Mn.

60. The method of claim 59, wherein the G1F oligosaccharide content of the anti-CD38 antibody is between 15% and 25%, the G0F oligosaccharide content of the anti-CD38 antibody is between 68% and 74%, and the culture medium is prepared to comprise between 4.0 ppb and 6.5 ppb Mn.

61. The method of claim 60, wherein the G1F oligosaccharide content of the anti-CD38 antibody is between 21% and 25%, the G0F oligosaccharide content of the anti-CD38 antibody is between 68% and 74%, and the culture medium is prepared to comprise between 5.0 ppb and 6.5 ppb Mn.

62. The method of claim 50, wherein the culture medium is a basal medium or a feed medium.

63. The method of claim 62, wherein culturing comprises a fed-batch culture or a perfusion culture.

64. The method of claim 63, wherein the host cell is an eukaryotic cell.

65. The method of claim 64, wherein the eukaryotic cell is a CHO cell, a PER.C6 cell, a NS0 cell, a Sp2/0 cell or a BHK cell.

66. The method of claim 65, wherein the CHO cell is a CHO-K1 cell, a CHO-DG44 cell, a CHO-S cell or a CHO-DXB11 cell.

67. The method of claim 66, wherein the CHO cell is deficient in glutamine synthetase (GS).

68. The method of claim 50, wherein the method is conducted under GMP-compliant conditions.

69. The method of claim 68, wherein the anti-CD38 antibody comprises the VH of SEQ ID NO: 7 and the VL of SEQ ID NO: 8.

70. The method of claim 69, wherein the anti-CD38 antibody comprises an IgG1 isotype.

71. The method of claim 70, wherein the anti-CD38 antibody comprises the HC of SEQ ID NO: 9 and the LC of SEQ ID NO: 10.

72. The method of claim 50, wherein the anti-CD38 antibody is a biosimilar.

73. The method of claim 50, wherein formulating the drug product comprises formulating the anti-CD38 antibody at from 20 mg/mL to 180 mg/mL with recombinant human hyaluronidase (rHuPH20) in an amount of from 30,000 U to 45,000 U, histidine at a concentration of from 5 mM to 15 mM, sorbitol at a concentration of from 100 mM to 300 mM, PS-20 at a concentration of from 0.01% w/v to 0.04% w/v and methionine at a concentration of from 1 mg/mL to 2 mg/mL, at a pH of 5.0 to 6.0.

74. The method of claim 73, wherein formulating the drug product comprises formulating the anti-CD38 antibody at 120 mg/mL in 2,000 U/ml recombinant human hyaluronidase (rHuPH20), 5 mM to 15 mM histidine, 100 mM to 300 mM sorbitol, 0.01% w/v to 0.04% w/v PS-20 and 1 mg/mL to 2 mg/mL methionine, at a pH of 5.6.

75. The method of claim 50, wherein formulating the drug product comprises formulating the anti-CD38 antibody at 20 mg/ml in 25 mM acetic acid, 60 mM sodium chloride, 140 mM mannitol and 0.04% w/v polysorbate-20 (PS-20); at pH 5.5.

76. The method of claim 50, wherein the culture medium is prepared to comprise between 2 ppb and 6.5 ppb Mn.

77. The method of claim 50, wherein the anti-CD38 antibody is daratumumab.

\* \* \* \* \*